US011154671B2

(12) United States Patent
Armistead et al.

(10) Patent No.: US 11,154,671 B2
(45) Date of Patent: Oct. 26, 2021

(54) NASAL DEVICES

(71) Applicant: ASAP Breatheassist Pty Ltd, Armadale (AU)

(72) Inventors: Justin Robert Armistead, The Basin (AU); Michael Ralph Burgess Johnson, Hawthorn (AU); Toby James Hartley, Ferntree Gully (AU)

(73) Assignee: ASAP Breatheassist Pty Ltd, Armadale (AU)

( * ) Notice: Subject to any disclaimer, the term of this patent is extended or adjusted under 35 U.S.C. 154(b) by 788 days.

(21) Appl. No.: 15/748,698

(22) PCT Filed: Jul. 14, 2016

(86) PCT No.: PCT/AU2016/050621
§ 371 (c)(1),
(2) Date: Jan. 9, 2019

(87) PCT Pub. No.: WO2017/020068
PCT Pub. Date: Feb. 9, 2017

(65) Prior Publication Data
US 2019/0117916 A1    Apr. 25, 2019

(30) Foreign Application Priority Data

Jul. 31, 2015 (AU) ................................ 2015903056

(51) Int. Cl.
*A61M 15/08* (2006.01)
*A61B 5/00* (2006.01)
(Continued)

(52) U.S. Cl.
CPC ............... *A61M 15/08* (2013.01); *A61B 5/08* (2013.01); *A61B 5/4818* (2013.01);
(Continued)

(58) Field of Classification Search
CPC ... A61B 2562/0247; A61B 5/08; A61B 5/087; A61B 5/091; A61B 5/4818;
(Continued)

(56) References Cited

U.S. PATENT DOCUMENTS

| 851,048   | A | 4/1907 | Woodward |
| 1,034,566 | A | 8/1912 | Barratt  |

(Continued)

FOREIGN PATENT DOCUMENTS

| AU | 2013204827 A1 | 2/2014 |
| AU | 2013205674 A1 | 2/2014 |

(Continued)

OTHER PUBLICATIONS

International Preliminary Report on Patentability in Int. Appln. No. PCT/AU2016/050621, completed Nov. 21, 2017, 22 pages.

(Continued)

*Primary Examiner* — Annette Dixon
(74) *Attorney, Agent, or Firm* — Servilla Whitney LLC

(57) ABSTRACT

A nasal device comprises a first component and a second component and a connector for coupling the first component to the second component and configured to span a nasal septum of the user. The first component comprises a body for insertion into a nasal cavity of a nose of a user. The body comprises a loop structure having an inner surface defining an aperture and a reverse outer surface, the loop structure being configured for alignment with an interior contour of a nasal passage of the nose, a platform spanning the aperture defined by the inner surface of the loop structure, and a valve mechanism disposed on the platform for controlling fluid flow through the aperture. The first component further comprises at least one mount extending from the body.

20 Claims, 11 Drawing Sheets

(51) Int. Cl.
  *A63B 23/18* (2006.01)
  *A61M 16/06* (2006.01)
  *A61B 5/08* (2006.01)
  *A61M 16/20* (2006.01)
  *A61F 5/56* (2006.01)
  *A61M 15/00* (2006.01)
  *A61M 16/08* (2006.01)
  *A61B 5/091* (2006.01)
  *A61B 5/087* (2006.01)

(52) U.S. Cl.
  CPC ............ *A61B 5/6819* (2013.01); *A61F 5/56* (2013.01); *A61M 15/002* (2014.02); *A61M 15/085* (2014.02); *A61M 16/0672* (2014.02); *A61M 16/208* (2013.01); *A63B 23/18* (2013.01); *A61B 5/087* (2013.01); *A61B 5/091* (2013.01); *A61B 2562/0247* (2013.01); *A61M 16/0666* (2013.01); *A61M 16/0858* (2014.02); *A61M 2205/3331* (2013.01); *A61M 2205/3368* (2013.01); *A61M 2209/088* (2013.01); *A61M 2210/0618* (2013.01); *A61M 2230/40* (2013.01)

(58) Field of Classification Search
  CPC ............ A61B 5/6819; A61F 5/08; A61F 5/56; A61M 15/002; A61M 15/02; A61M 15/08; A61M 15/085; A61M 16/0666; A61M 16/0672; A61M 16/0688; A61M 16/0816; A61M 16/0841; A61M 16/0858; A61M 16/105; A61M 16/107; A61M 16/20; A61M 16/208; A61M 2016/0021; A61M 2016/0036; A61M 2202/0208; A61M 2205/0216; A61M 2205/0238; A61M 2205/0266; A61M 2205/3306; A61M 2205/3331; A61M 2205/3368; A61M 2209/088; A61M 2210/0618; A61M 2230/40; A61M 29/00; A61M 3/0262; A62B 23/06; A62B 7/10; A62B 9/06; A63B 2208/03; A63B 23/18; A63B 33/00; Y10S 55/35
  See application file for complete search history.

(56) References Cited

U.S. PATENT DOCUMENTS

| | | |
|---|---|---|
| 1,077,574 A | 11/1913 | Woodward |
| 1,255,578 A | 2/1918 | Boxley |
| 1,481,581 A | 1/1924 | Woodward |
| 2,243,360 A | 5/1941 | Slatis et al. |
| 3,710,799 A | 1/1973 | Caballero |
| 3,722,509 A | 3/1973 | Nebel |
| 3,905,335 A | 9/1975 | Kapp |
| 4,414,977 A | 11/1983 | Rezakhany |
| 4,576,168 A | 3/1986 | Jalowayski |
| 4,592,357 A | 6/1986 | Ersek |
| 4,759,365 A | 7/1988 | Askinazy |
| 5,059,193 A | 10/1991 | Kuslich |
| 5,099,857 A | 3/1992 | Baldo et al. |
| 5,423,858 A | 6/1995 | Bolanos et al. |
| RE35,408 E | 12/1996 | Petruson |
| 5,683,465 A | 11/1997 | Shinn et al. |
| 5,693,100 A | 12/1997 | Pisharodi |
| 5,787,884 A | 8/1998 | Tovey |
| 5,895,409 A | 4/1999 | Mehdizadeh |
| 5,931,852 A | 8/1999 | Brennan |
| 5,955,376 A | 9/1999 | Tovey |
| 6,109,262 A | 8/2000 | Tovey |
| 6,129,763 A | 10/2000 | Chauvin et al. |
| 6,270,512 B1 | 8/2001 | Rittmann |
| 6,436,142 B1 | 8/2002 | Paes et al. |
| 6,561,188 B1 * | 5/2003 | Ellis ............ A61M 3/0262 128/203.22 |
| 6,562,057 B2 | 5/2003 | Santin |
| 6,626,179 B1 | 9/2003 | Pedley |
| 6,821,298 B1 | 11/2004 | Jackson |
| 6,978,781 B1 | 12/2005 | Jordan |
| 7,055,523 B1 | 6/2006 | Brown |
| 7,105,008 B2 | 9/2006 | Maryanka |
| 7,108,198 B2 | 9/2006 | Altadonna, Jr. |
| 7,318,438 B2 | 1/2008 | Brown |
| 7,390,331 B2 | 6/2008 | Santin et al. |
| D575,397 S | 8/2008 | Noce |
| 7,461,651 B2 | 12/2008 | Brown |
| 7,727,252 B2 | 6/2010 | Maryanka |
| 7,740,643 B2 | 6/2010 | Maryanka |
| 7,918,224 B2 | 4/2011 | Dolezal et al. |
| 8,048,102 B2 | 11/2011 | Brown |
| D652,143 S | 1/2012 | Brown |
| 8,262,688 B2 | 9/2012 | Santin et al. |
| 8,403,954 B2 | 3/2013 | Santin et al. |
| 8,491,622 B2 | 7/2013 | Brown |
| 8,833,369 B2 | 9/2014 | Dolezal et al. |
| 8,834,512 B1 | 9/2014 | Brown et al. |
| D726,312 S | 4/2015 | Johnson |
| D819,205 S | 5/2018 | Snyder |
| 2002/0029004 A1 | 3/2002 | Starr et al. |
| 2003/0086825 A1 | 5/2003 | Brennan |
| 2003/0106555 A1 | 6/2003 | Tovey |
| 2003/0144684 A1 | 7/2003 | Ogle |
| 2004/0079814 A1 | 4/2004 | Altadonne, Jr. |
| 2004/0111109 A1 | 6/2004 | Ruiz |
| 2005/0021073 A1 | 1/2005 | Santin et al. |
| 2005/0278028 A1 | 12/2005 | Mujwid |
| 2006/0185676 A1 | 8/2006 | Brown |
| 2006/0185677 A1 | 8/2006 | Brown |
| 2006/0207598 A1 | 9/2006 | Brown |
| 2006/0259064 A1 | 11/2006 | Maryanka |
| 2006/0266367 A1 | 11/2006 | Noce |
| 2007/0107731 A1 | 5/2007 | Reed |
| 2008/0167676 A1 | 7/2008 | Howard |
| 2008/0178873 A1 | 7/2008 | Alpers |
| 2009/0194100 A1 * | 8/2009 | Minagi ............ A61F 5/08 128/200.24 |
| 2009/0198268 A1 | 8/2009 | Case |
| 2010/0042134 A1 | 2/2010 | Wien |
| 2010/0063523 A1 | 3/2010 | Menard et al. |
| 2010/0063532 A1 | 3/2010 | Moore |
| 2010/0087749 A1 | 4/2010 | Tovey |
| 2011/0118775 A1 | 5/2011 | Brown |
| 2012/0111340 A1 | 5/2012 | Robitaille |
| 2012/0279504 A1 | 11/2012 | Moore |
| 2012/0330176 A1 | 12/2012 | Leow |
| 2012/0330345 A1 | 12/2012 | Tasca |
| 2013/0081637 A1 * | 4/2013 | Foley ............ A61F 5/56 128/848 |
| 2013/0081639 A1 | 4/2013 | Borjegren et al. |
| 2013/0211275 A1 * | 8/2013 | Curti ............ A61M 16/0057 600/543 |
| 2013/0296809 A1 | 11/2013 | Santin et al. |
| 2014/0128761 A1 | 5/2014 | Cline et al. |
| 2014/0128904 A1 | 5/2014 | Mezzoli et al. |
| 2014/0246023 A1 | 9/2014 | Maryanka |
| 2015/0000675 A1 | 1/2015 | Kallikounis et al. |
| 2015/0196420 A1 | 7/2015 | Ede et al. |

FOREIGN PATENT DOCUMENTS

| | | |
|---|---|---|
| CA | 2566268 A1 | 11/2004 |
| CN | 101166555 A | 4/2008 |
| CN | 103520815 A | 1/2014 |
| EP | 1917993 A1 | 5/2008 |
| EP | 2387978 A2 | 11/2011 |
| EP | 2114326 B1 | 3/2014 |
| EP | 1968684 B1 | 2/2016 |
| JP | H032259 A | 1/1991 |
| JP | H1142285 A | 2/1999 |
| JP | H11192251 A | 7/1999 |
| JP | 3024536 B2 | 3/2000 |

(56) References Cited

FOREIGN PATENT DOCUMENTS

| | | |
|---|---|---|
| JP | 2011189050 A | 9/2011 |
| KR | 100893945 B1 | 4/2009 |
| WO | 88/09149 A1 | 12/1988 |
| WO | 96/06657 A1 | 3/1996 |
| WO | 96/07099 A1 | 3/1996 |
| WO | 99/36773 A1 | 7/1999 |
| WO | 00/78223 A1 | 12/2000 |
| WO | 01/62342 A1 | 8/2001 |
| WO | 02/31465 A1 | 4/2002 |
| WO | 02/059569 A1 | 8/2002 |
| WO | 2004026391 A1 | 4/2004 |
| WO | 2007119041 A1 | 10/2007 |
| WO | 2007139890 A2 | 12/2007 |
| WO | 2008/091782 A2 | 7/2008 |
| WO | 2008109873 A2 | 9/2008 |
| WO | 2009/124567 A1 | 10/2009 |
| WO | 2010031040 A2 | 3/2010 |
| WO | 2011/104660 A2 | 9/2011 |
| WO | 2012/137182 A2 | 10/2012 |
| WO | 2014015359 A1 | 1/2014 |
| WO | 2014042862 A1 | 3/2014 |

OTHER PUBLICATIONS

International Search Report in Int. Appln. No. PCT/AU2016/050621, dated Oct. 25, 2016, 7 pages.
Written Opinion of the International Searching Authority in Int. Appln. No. PCT/AU2016/050621, dated Oct. 25, 2016, 7 pages.
International Preliminary Report on Patentability in PCT/AU2014/000649, dated Oct. 12, 2016, 5 pages.
International Preliminary Report on Patentability in PCT/AU2015/050032, dated Dec. 20, 2016, 4 pages.
International Search Report in International Application No. PCT/AU2015/050314, dated Aug. 12, 2015, 4 pages.
International Search Report in PCT/AU2014/000649, dated Sep. 18, 2014, 7 pages.
International Search Report in PCT/AU2015/050032, dated Apr. 17, 2015, 5 pages.
Non-Final Office Action in U.S. Appl. No. 15/319,940, dated Apr. 6, 2018, 41 pages.
Non-Final Office Action in U.S. Appl. No. 15/319,941, dated Apr. 11, 2018, 50 pages.
Written Opinion of the International Searching Authority in International Application No. PCT/AU2015/050314, dated Aug. 12, 2015, 4 pages.
Written Opinion of the International Searching Authority in PCT/AU2014/000649, dated Sep. 18, 2014, 7 pages.
Written Opinion of the international Searching Authority in PCT/AU2015/050032, dated Apr. 17, 2015, 3 pages.
Airware Labs, retrieved from the internet Jul. 9, 2018, <URL: https://web.archive.org/web/20120522113321/http://www.airwarelab.com/>, published Mar. 22, 2012, 5 pages.
Breathe EZ Anti-Snoring Medical Nasal Device—Snoring Cure, retrieved from the internet on Jul. 9, 2018, <URL: https://web.archive.org/web/20120618221246/http://www.snoringcure.ca/breathe_ez_nasal_anti_snoring_medical_device.htm>, published May 14, 2007, 1 page.
Breathe-Aide, retrieved from the internet Jul. 9, 2018, <URL: https://web.archive.org/web/20141108204923/http://breatheaide.fm.alibaba.com/>, published Nov. 8, 2014, 1 page.
Breathe-Ezy Nasal Filters, retrieved from the internet Jul. 8, 2018, <URL: https://web.archive.org/web/20120615192635/http://www.breathe-ezy.com.au/>, published Apr. 29, 2005, 6 pages.
Breathing Relief Nasal Dilator, retrieved from the internet Jul. 9, 2018, <URL: https://web.archive.org/web/20120413210250/http://www.breathingrelief.com/>, published Jun. 16, 2006, 2 pages.
ClipAir® Anti-Snoring Nasal Dilator Device/Contre le Ronflement, retrieved from the internet on Jul. 9, 2018, <URL: https://web.archive.org/web/20120618061055/http://www.snoringcure.ca/clipair_nasal_anti_snoring_medical_dilator_device.htm>, published Aug. 1, 2010, 2 pages.
Flents Breathe Quiet! Nasal Dilator—Stop Snoring!, retrieved from the internet on Jul. 9, 2018, <URL: https://web.archive.org/web/20120425220535/http://www.amazon.com/Flents-Breathe-Quiet-Nasal-Dilator/dp/B00191HLR2>, published Aug. 29, 2010, 4 pages.
Flents Breathe Well Nasal Dilator—The Alternative to Nasal Strips, retrieved from the internet Jul. 9, 2018, <URL: https://web.archive.org/web/20120411195907/http://www.amazon.com/Flents-Breathe-Well-Nasal-Dialator/dp/B001J4K5E2>, published Feb. 2, 2009, 4 pages.
Inhalclip, retrieved from the internet Jul. 9, 2018, <URL: https://web.archive.org/web/20120413113017/http://www.oscimedsa.com/Stress_insomnie_stop>, published Oct. 21, 2010, 3 pages.
International Preliminary Examination Report in PCT/AU2003/000504 dated Feb. 2, 2005, 36 pages.
Max-Air Nose Cones, retrieved from the internet Jul. 9, 2018, <URL: https://web.archive.org/web/20120725110753/http://www.maxairnosecones.com/max-air-nose-cones>, published Feb. 13, 2011, 8 pages.
Megavent Nasal Dilator, retrieved from the internet Jul. 9, 2018, <URL: http://www.wellnessproducts.ch/?lan=en&page=2&id=66999>, published Jun. 26, 2012, 3 pages.
Nasal Pass Dilator retrieved from the internet Jul. 9, 2018, <URL: https://web.archive.org/web/20120630121946/http://nasalpass.com/contact_us.htm>, published Apr. 21, 2006, 1 pages.
Nasilator, The Science of Better Breating, retrieved from the internet Jul. 17, 2018, <URL: https://web.archive.org/web/20121219024329/http://www.nasilator.com/home.aspx>, published Sep. 6, 2012, 1 pages.
Non-Final Office Action in U.S. Appl. No. 10/631,415 dated Aug. 18, 2005, 15 pages.
Non-Final Office Action in U.S. Appl. No. 10/631,415 dated Dec. 29, 2005, 9 pages.
Non-Final Office Action in U.S. Appl. No. 11/363,884 dated May 14, 2009, 9 pages.
Non-Final Office Action in U.S. Appl. No. 11/363,924 dated Apr. 13, 2009, 9 pages.
Non-Final Office Action in U.S. Appl. No. 12/154,868 dated Oct. 23, 2014, 35 pages.
Noseglobes, retrieved from the internet Jul. 9, 2018, <URL:https://web.archive.org/web/20110128162352/http://noseglobes.com/>, published Jan. 28, 2011, 1 page.
Nozovent® Anti-Snoring Medical Nasal Dilator Device, retrieved from the internet on Jul. 9, 2018, <URL: https://web.archive.org/web/20120619012956/http://www.snoringcure.ca/nozovent_nasal_anti_snoring_medical_dilator_device.htm>, published Jul. 13, 2007, 2 pages.
Original Breathe Fit Snoring Aid Nasal Dilator, by Breathe Fit Nasal Dilator, retrieved from the internet on Jul. 9, 2018, <URL: https://web.archive.org/web/20120619035547/http://www.amazon.com/Original-Breathe-Fit-Nasal-Dilator/dp/B0012RMWC4>, published Aug. 21, 2009, 5 pages.
Sanispira Dpi, retrieved from the internet Jul. 9, 2018, <URL: https://web.archive.org/web/20120712044423/http://www.sanispira.it/eng/index.php>, published Mar. 4, 2011, 3 pages.
Sinus Cones, retrieved from the internet Jul. 9, 2018, <URL: https://web.archive.org/web/20120206054639/http://www.sanostec.com/code/productinfo.htm>, published Sep. 8, 2004, 2 pages.
SleepRight, retrieved from the internet Jul. 11, 2018, <URL: http://www.sleepright.com/nasal-breathe-aid.php>, published Jun. 17, 2013, 6 pages.
Snore Free, retrieved from the internet Jul. 9, 2018, <URL: https://web.archive.org/web/20120614222005/http://www.magnetictherapy.co.uk/scp/SPECIALITY_PRODUCTS/SNORE_FREE.html>, published Dec. 8, 2004, 2 pages.
Snore Pin, Sleep Apnea Snoring Treatment, retrieved from the internet Jul. 17, 2018, <URL: https://web.archive.org/web/20130111010828/http://omnisleep.in/snore-pin.html>, published Jan. 11, 2013, 2 pages.
Snoreben, retrieved from the internet Jul. 9, 2018, <URL: http://www.benmedical.com.au/>, published Jan. 2011, 2 pages.

(56) References Cited

OTHER PUBLICATIONS

Snoregem, British Snoring & Sleep Apnoea Associate, retrieved from the internet Jul. 9, 2018, <URL: https://web.archive.org/web/20120627060249/http://www.britishsnoring.co.uk/shop/snoregem.php>, published Jul. 3, 2010, 2 pages.

Snore-no-More, retrieved from the internet Jul. 9, 2018, <URL: https://web.archive.org/web/20120626140524/http://www.britishsnoring.co.uk/shop/nasal_dilators/snore_no_more.php?>, published Dec. 12, 2005, 1 pages.

Surgical Nostril Retainers, Porex Surgical Products Group, retrieved from the internet Jul. 17, 2018, <URL: https://web.archive.org/web/20051217233845/https://www.porexsurgical.com/English/surgical/sprodnoseother.asp>, published Dec. 19, 2005, 2 pages.

Ultimate Nasal Dilator, retrieved from the internet Jul. 9, 2018, <URL: https://web.archive.org/web/20120718070024/http://www.nasalaid.com/>, published Oct. 28, 2007, 1 page.

WoodyKnows—Super Nasal Filter for Allergy Relief, retrieved from the internet Jul. 17, 2018, <URL: https://web.archive.org/web/20120818163139/http://www.woodyknows.com:80/>, published Aug. 18, 2012, 3 pages.

Final Office Action in U.S. Appl. No. 15/319,940 dated Jan. 7, 2020, 25 pages.

Final Office Action in U.S. Appl. No. 15/319,941 dated Mar. 3, 2020, 41 pages.

Non-Final Office Action in U.S. Appl. No. 15/579,304 dated Jan. 24, 2020, 21 pages.

Non-Final Office Action in U.S. Appl. No. 15/579,304 dated Aug. 21, 2020, 12 pages.

Non-Final Office Action in U.S. Appl. No. 15/319,940 dated Sep. 30, 2020, 20 pages.

Non-Final Office Action in U.S. Appl. No. 15/319,941 dated Sep. 30, 2020, 17 pages.

Final Office Action in U.S. Appl. No. 15/579,304, dated Jan. 21, 2021, 13 pages.

\* cited by examiner

NASAL DEVICES

CROSS REFERENCE TO RELATED APPLICATIONS

This is a National Phase entry of International Application No. PCT/AU2016/050621, filed Jul. 14, 2016, which claims priority to Australian Patent Application No. 2015903056, filed Jul. 31, 2015, the disclosures of which are incorporated herein by reference in their entireties.

TECHNICAL FIELD

Described embodiments relate generally relate to nasal devices, for example, intranasal positive expiratory airway pressure (INPEAP) devices. Some embodiments relate to nasal devices configured to receive or accommodate one or more conduits and/or sensors to allow for the gathering of data and/or the delivery or removal of fluids or drugs.

BACKGROUND

Obstructive Sleep Apnoea (OSA) is a condition that is highly prevalent in the general population. OSA is characterised by repetitive occlusion of the upper airway during sleep causing reduction in airflow leading to hypoxia and/or arousals. This may result in fragmented sleep, daytime somnolence, impaired cognitive function and adverse cardiovascular outcomes. Continuous positive airway pressure (CPAP) devices, such as airway pressure ventilators, and mandibular splint devices are known to ameliorate OSA. However, many such devices are invasive and tend to be only marginally effective.

It is desired to address or ameliorate one or more shortcomings of known devices, or to at least provide a useful alternative thereto.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

SUMMARY

Some embodiments relate to a nasal device comprising: a first component and a second component; and a connector for coupling the first component to the second component and configured to span a nasal septum of the user; wherein the first component comprises: a body for insertion into a nasal cavity of a nose of a user, the body comprising: a loop structure having an inner surface defining an aperture and a reverse outer surface, the loop structure being configured for alignment with an interior contour of a nasal passage of the nose; a platform spanning the aperture defined by the inner surface of the loop structure; and a valve mechanism disposed on the platform for controlling fluid flow through the aperture; and at least one mount extending from the body.

The valve mechanism may comprise a seal spanning the aperture defined by the inner surface of the loop structure, wherein the seal includes a valve configured to transition between an open state, whereby fluid may be conveyed through the platform, and a closed state, whereby fluid may be hindered from being conveyed through the platform by the valve. In some embodiments, an orifice may be disposed in the seal.

In some embodiments, a conduit aperture may be disposed in the body and a first mount of the at least one mount may be configured to cooperate with the conduit aperture to facilitate passage of fluid between the conduit aperture and a conduit supported by the at least one mount. The conduit aperture may be configured to cooperate with the first mount to accommodate passage of the conduit through the body and into the nasal cavity. The conduit aperture may be configured to cooperate with the first mount to accommodate passage of a coupler through the body and into the nasal cavity, wherein the coupler may be configured to couple the first mount to the conduit. The conduit aperture may be disposed in the platform and extends there through. The conduit aperture may be disposed in the loop structure and may extend from a first side of the loop structure to a reverse second side of the loop structure.

In some embodiments, the at least one mount may comprise a second mount extending from the body and arranged to support one or more conduits, wherein the second mount may be configured to position an open end of the conduit in proximity to the nasal cavity. The at least one mount may comprise a second mount extending from the body and arranged to support one or more conduits, wherein the second mount may be configured to position an open end of a coupler in proximity to the nasal cavity, wherein the coupler is configured to couple the second mount to the conduit.

In some embodiments, the first component may further comprise a mount assembly extending from the body and wherein the at least one mount may be supported by the mount assembly. In some embodiments, the first component may further comprise a mount assembly for supporting the at least one mount, the mount assembly having an inner passage extending through the mount assembly and the mount assembly being disposed on the body to allow for fluid communication between the orifice disposed in the platform and the inner passage. A first mount of the at least one mount may project from the mount assembly, the first mount having an inner passage extending through the first mount and configured to cooperate with a conduit aperture disposed in the body to facilitate passage of fluid between the conduit aperture and a conduit supported by the first mount. The inner passage of the first mount may be configured to cooperate with the conduit aperture to accommodate passage of the conduit through the body and into the nasal cavity. The inner passage of the first mount may be configured to cooperate with the conduit aperture to accommodate passage of a coupler through the body and into the nasal cavity, wherein the coupler may be configured to couple the first mount to the conduit.

In some embodiments, a second mount of the at least one mount may project from the mount assembly, the second mount having an inner passage extending through the second mount and the inner passage of the second mount being in fluid communication with the inner passage of the mount assembly.

In some embodiments, the mount assembly may comprise a collar having a first end coupled to the body, the collar spanning the aperture defined by the inner surface of the loop structure and providing fluid communication between the aperture and the inner passage of the mount assembly.

The collar may comprise a tapering section coupled to the body and an end section extending from the tapering section away from the body. The tapering section may form a seal with at least one of the loop structure, the valve mechanism and the platform.

In some embodiments, the body may further comprise an arm member having a first end coupled to the loop structure and a free end, the arm member extending outwardly from the loop structure and configured to extend along a nasal passage of the nasal cavity and engage with an internal surface of a nostril of the nose. The connector may comprises a leg member extending outwardly from the loop structure and configured to protrude from the nasal cavity of the user, and wherein the arm member extends from a first side of the loop structure and the leg member extends from the reverse second side of the loop structure. The connector may comprise a substantially u-shaped clip or a tether.

The loop structure may comprise an outer layer disposed along at least a portion of the outer surface of the loop structure. The outer layer may be a deformable material comprising at least one of memory foam, an overmould, and an inflatable tube. The outer layer may comprise at least one protruding flange portion extending along at least a section of the outer surface of the loop structure. The outer layer may be infused with at least one of a compound, a medicament, a fragrance, and an aromatic agent. A film including a compound may be disposed on the loop structure and may be provided with a removable seal to mitigate release of the compound from the film. A coating may be disposed on the loop structure and may be arranged to release a scent in response to abrasion of the coating.

In some embodiments, the second component may be substantially identical to the first component. In some embodiments, the second component may be different from the first component. The second component may comprise a body for insertion into a nasal cavity of a nose of a user, the body comprising a loop structure having an inner surface defining an aperture and a reverse outer surface, the loop structure being configured for alignment with an interior contour of a nasal passage wall of the nose and a barrier which spans the aperture of the loop structure to mitigate the flow of fluid through the aperture.

In some embodiments, the at least one mount may be arranged to support at least one measurement mechanisms and/or fluid transfer mechanism. The at least one mount may be arranged to support at least one sensors and/or at least one conduits. The at least one mount may comprise at least one coupler to couple the at least one sensors and/or the at least one conduits to the at least one mount.

Some embodiments relate to a method of creating an intranasal positive expiratory airway pressure in a nasal cavity of a subject, the method comprising: inserting the bodies of respective first and second components of the nasal device as described above into respective nasal cavities of the subject such that the loop structure is aligned with an interior contour of a nasal passage of the nose and the valve mechanism is orientated to allow fluid flow through the valve in response to the subject inhaling and to substantially block fluid flow through the valve in response to the subject exhaling.

Some embodiments relate to a method of gathering of data from a user wearing the nasal device described above, the method comprising: coupling at least one cannula including at least one sensor to the at least one mount of a component of a nasal device; coupling the at least one cannula to a measurement device; inserting the components of the nasal device in respective nostril cavities of a user; detecting by the at least one sensor a breathing characteristic of the user; and determining by the measurement device a measurement indicative of the breathing characteristic.

Some embodiments relate to a method of delivering fluids to a nasal cavity of a user wearing the nasal device as described above, the method comprising: coupling at least one cannula to the at least one mount of a component of a nasal device; coupling the at least one cannula to a fluid delivery device; inserting the components of the nasal device in respective nostril cavities of a user; and delivering fluid from the fluid deliver device to the nasal cavity using the at least one cannula.

Some embodiments relate to a method of removing fluids from a nasal cavity of a user wearing the nasal device as described above, the method comprising: coupling at least one cannula to the at least one mount of a component of a nasal device; coupling the at least one cannula to a fluid removal device; inserting the components of the nasal device in respective nostril cavities of a user; removing fluid from the nasal cavity via the at least one cannula using the fluid removal device.

Some embodiments relate to use of the nasal device described above to treat a sleeping disorder, for example, sleep apnea.

BRIEF DESCRIPTION OF DRAWINGS

Embodiments are described in further detail below, by way of example, with reference to the accompanying drawings, in which.

DESCRIPTION OF EMBODIMENTS

Figure 1A:
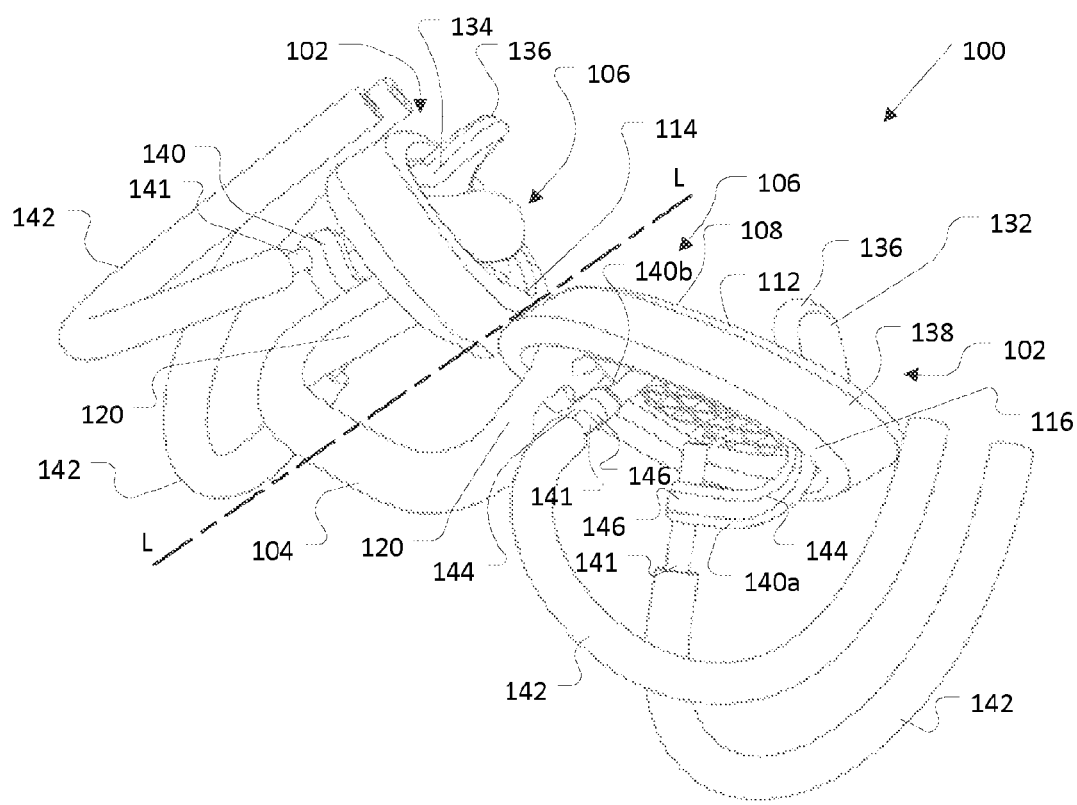
FIG. 1A is a front perspective view of a nasal device according to some embodiments.

Described embodiments generally relate to nasal devices, such as intranasal positive expiratory airway pressure (IN-PEAP) devices. Some embodiments relate to nasal devices configured to receive or accommodate one or more conduits and/or sensors to allow for the gathering of data and/or the delivery or removal of fluids and/or delivery of drugs. For example, gathered data may be employed for diagnosis purposes. In some embodiments, the nasal device may comprise one or more mounts arranged to receive or accommodate one or more conduits and/or sensors, and in some embodiments, the mounts may be supported by a mount assembly coupled to a body of the nasal device. In some embodiments, the one or more conduits may comprise one or more cannulas for delivering and/or removing fluid from the nasal cavity and/or gathering data. In some embodiments, the one or more conduits may comprise one or more pitot tubes or other suitable pressure measurement instrument for measuring breath characteristics, such as fluid flow velocity and fluid pressure.

Referring to FIGS. 1A to 1D, there is illustrated a nasal device, generally indicated at 100. The nasal device 100 comprises a component 102. In some embodiments the nasal device 100 comprises a first one of the component 102 coupled to a second one of the component 102. In some embodiments, the second component may be substantially identical to the first component. In some embodiments, the second component may be different from the first component.

In some embodiments, the first one of the component 102 (referred to in shorthand as the first component 102) may be coupled to the second one of the component 102 (referred to in shorthand as the second component 102) by a connector 104 configured to span a septum of a nose, in use. For example, and as depicted in FIGS. 1A to 1D, the connector 104 may comprise a substantially u-shaped portion. In other embodiments, the connector 104 may comprise a tether (not shown). As illustrated in FIGS. 1A to 1D, the first and second components 102, respectively, may substantially correspond with one another and the nasal device 100 may be substantially symmetrical about a longitudinal axis L of the connector 104. For example, the first component 102 may correspond with the second component 102. In other embodiments, the first component 102 may differ from the second component 102.

As depicted, at least one of the first and second components 102 may comprise a body 106 having a loop structure 108. The body 106 may be a intranasal body. The body 106 may be coupled to the connector 104 and the loop structure 108 may extend in a first plane P1 which forms a substantially acute angle, a substantially right angle or a substantially obtuse angle with a second plane P2 in which the connector 104 extends. In some embodiments, the connector 104 may extend along the longitudinal axis L in the second plane P2, and the loop structure 108 may extend outward from the longitudinal axis L in the first plane P1. The loop structure 108 of the first component 102 and loop structure 108 the second component 102 may extend away from one another.

The loop structure 108 may comprise an inner surface 110 and a reverse outer surface 112. For example, the inner surface 110 may be a first major surface of the loop structure 108 and the outer surface 112 may be a second major surface of the loop structure 108, opposite to or reverse from the first major surface. The loop structure 108 may further comprise a first side 114, or first minor surface, and a second side 116, or second minor surface, opposite to or reverse from the first side 114.

The inner surface 110 of the loop structure 108 defines an aperture 118. For example, the aperture may be substantially round, teardrop or oval in shape.

Figure 2A:
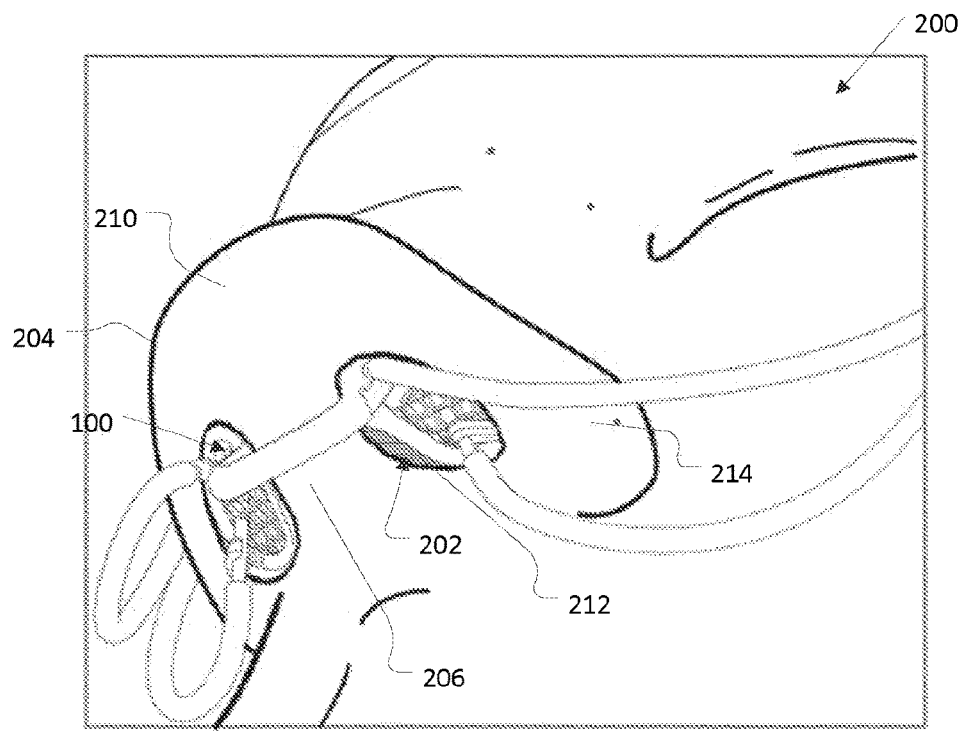
FIG. 2A is a perspective view of a user donning the nasal device of FIGS. 1A to 1D.
Figure 2B:
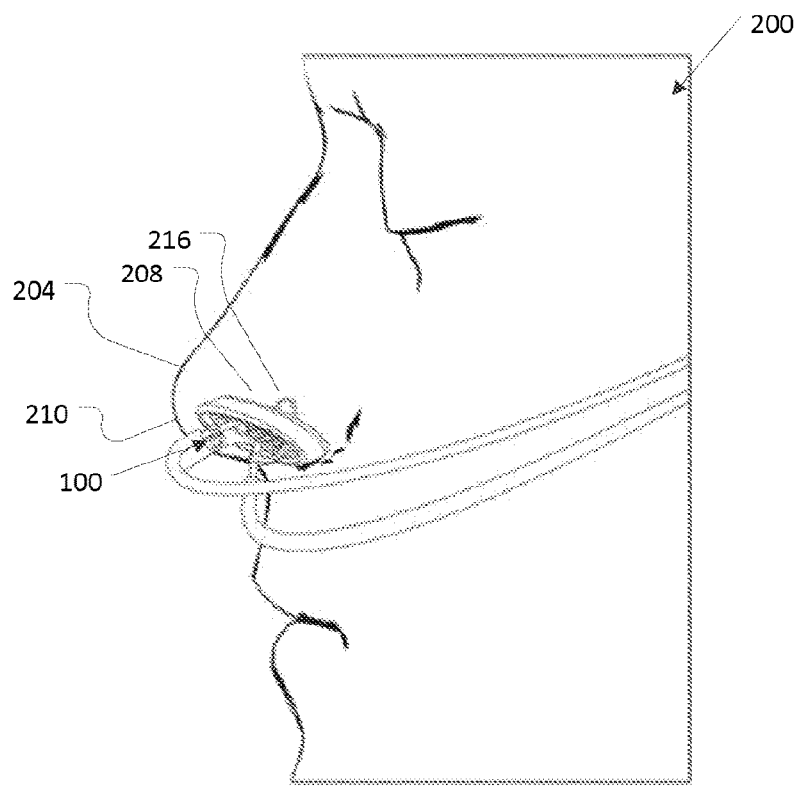
FIG. 2B is a side view of the user of FIG. 2A.
Figure 3A:
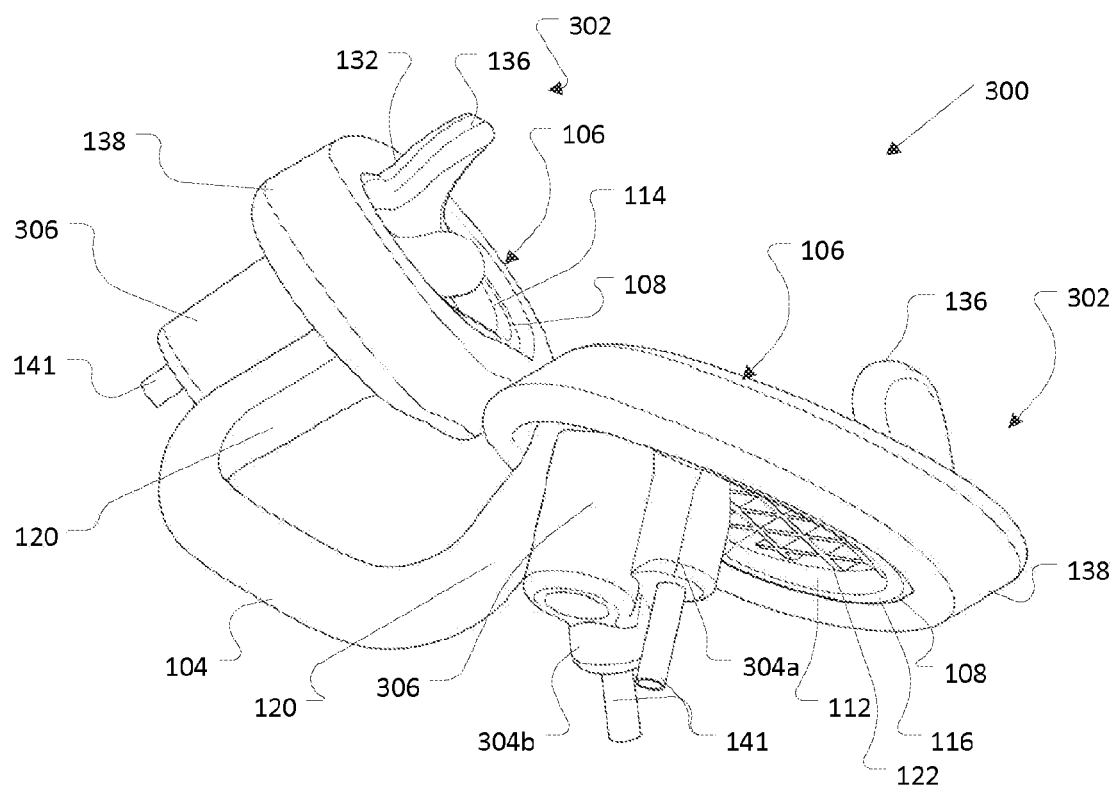
FIG. 3A is a front perspective view of a nasal device according to some embodiments.
Figure 3B:
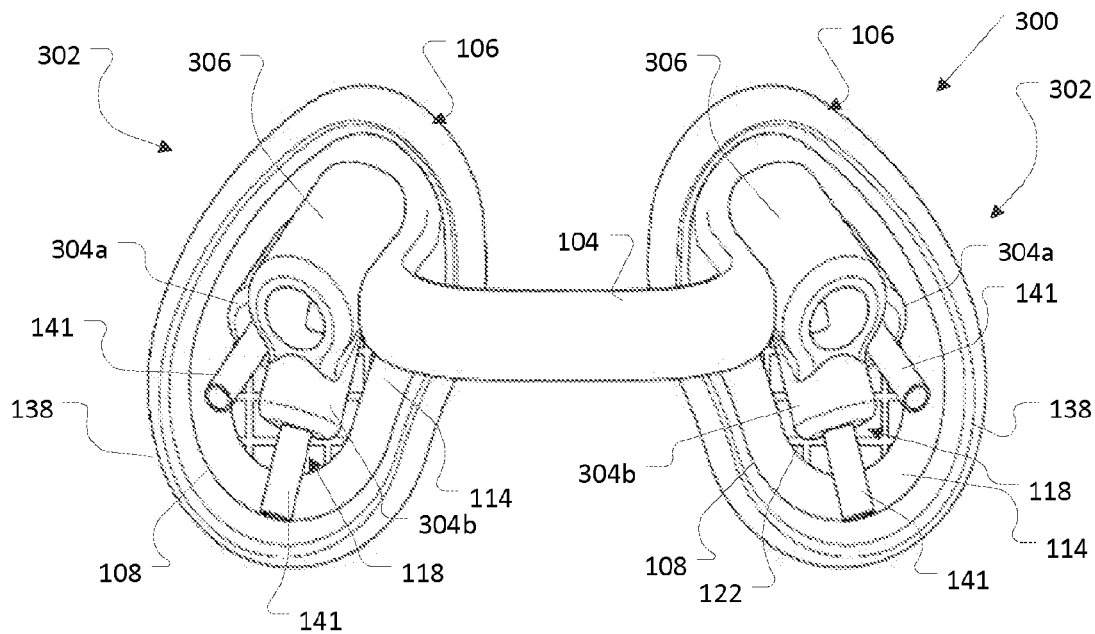
FIG. 3B is a front view of the nasal device of FIG. 3A.
Figure 3C:
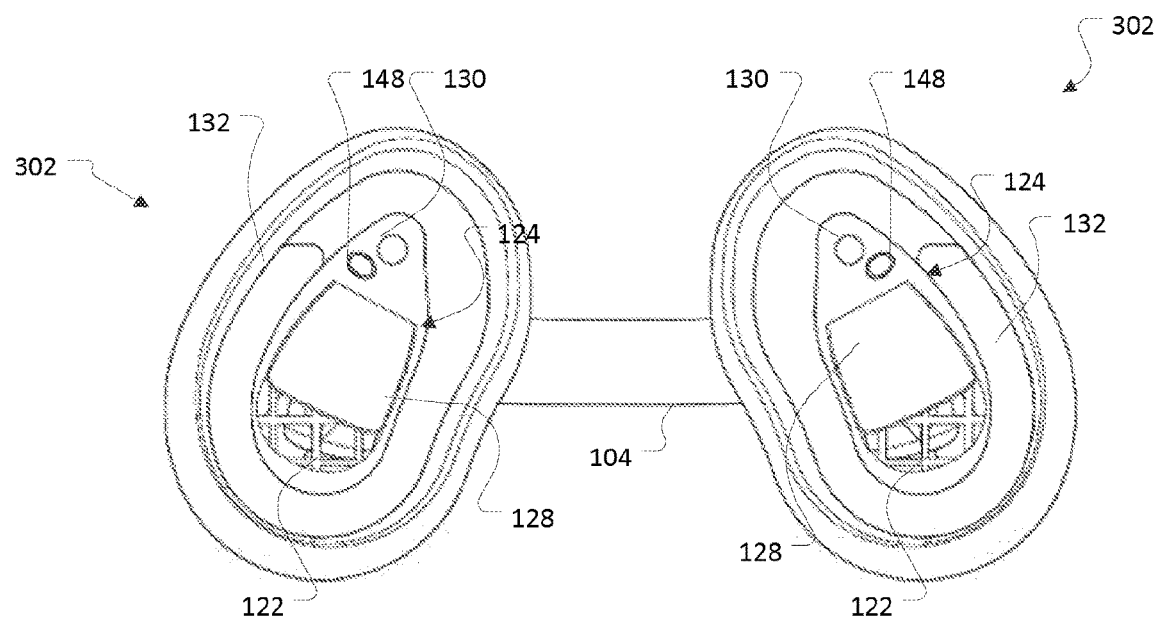
FIG. 3C is a back view of the nasal device of FIG. 3A.
Figure 3D:
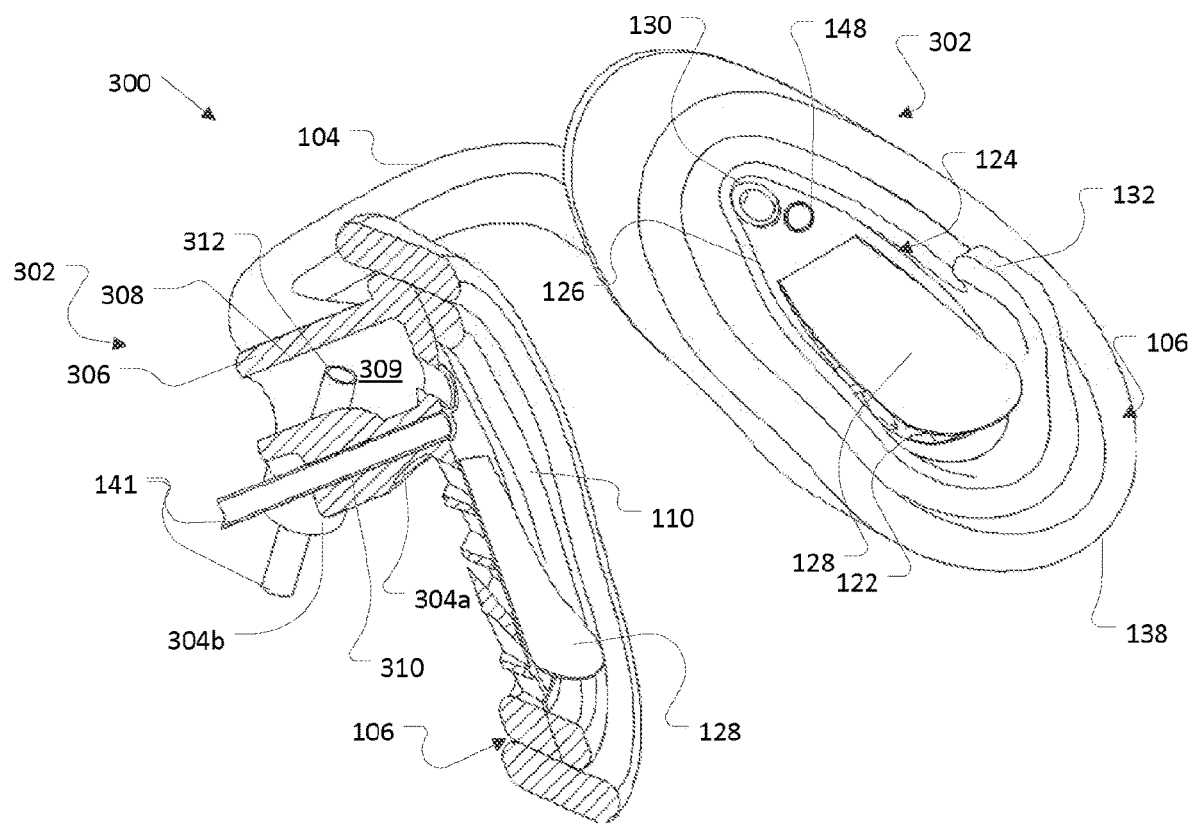
FIG. 3D is a back perspective view of the nasal device of FIG. 3A showing a cut away view of a component of the nasal device.

In use, the outer surface 112 of the loop structure 108 may be orientated to engage with the nasal passage wall 212 of the nasal cavity such that the loop structure 108 aligns with an interior contour of a nasal passage 208 of a nose 204 or coaxially aligns with the nasal passage wall 212 of the nasal cavity 202, as shown in FIGS. 2A and 2B. In some embodiments, the outer surface 112 of the loop structure 108 is configured to form a substantial seal with the nasal passage wall 212 of the nasal cavity 202. For example, the outer surface 112 of the loop structure 108 may be sized and configured to substantially form a seal with the nasal passage wall 212.

In some embodiments, the outer surface 112 of the loop structure 108 may be configured for urging against a nasal passage wall 212 of a nasal cavity 202 of a user 200. In some embodiments, the outer surface 112 of the loop structure 108 may be configured to follow a contour of the nasal cavity of the user and to urge against or exert an outward force on the nasal passage wall 212 of the nasal cavity 202 to thereby dilate nostrils 214 of the nose 204. Nasal device 100 (and any other embodiments described herein) may therefore be alternatively referred to as a nasal dilator or nasal dilator device.

In some embodiments, the first and second components 102 may comprise a leg member 120, which extends outwardly from the loop structure 108. In some embodiments, the leg member 120 may extend from the second side 116 of the loop structure 108. The leg member 120 may be configured to protrude from the nose 204 of the user 200 in use and may be employed to hold the nasal dilator 100 and to position and adjust the nasal dilator 100 in the nasal cavity 202 of the nose 204, as shown in FIGS. 2A and 2B. In some embodiments, the connector 104 is coupled to or integrally formed with the leg member 120.

In some embodiments, one or both of the component 102 of the nasal dilator device 100 comprise a platform 122 spanning the aperture 118 defined by the inner surface 110 of the loop structure 108. For example, the platform 122 may comprise a mesh and/or a latticed structure. In some embodiments, the platform 122 may be releaseably coupled or attached to the inner surface 110 of the loop structure 108, for example, by a snap fit or interference fit.

In some embodiments, the platform 122 may comprise a filter (not shown) which may be composed of a fine woven mesh or an open celled porous material, such as a foam or compressed fibre. For example, the filter (not shown) may be employed to filter out airborne particles such as bacteria, dust, pollens, and/or other allergens. In some embodiments, the filter (not shown) may be replaceable and may be arranged to be removeably connected, or "snap-fit" to the inner surface 110 of the loop structure 108. Alternatively, the filter (not shown) may be integrally formed with, or may be welded or ultrasonically welded to the loop structure 108.

As shown in FIGS. 1A to 1D, the body 106 may comprise a valve mechanism 124 to allow for control of flow of fluid, such as air, through the aperture 118 defined by the inner surface 110 of the loop structure 108. In some embodiments, the valve mechanism 124 may comprise a cover portion or seal 126 supported by the platform 122 and which may span the aperture 118 of the loop structure 108. The cover portion 126 may form a seal with the inner surface 110 of the loop structure 108. The cover portion 126 may comprise a valve or flap 128 configured to transition between an open state, whereby fluid, such as air, may be conveyed through the platform 122 and a closed state, whereby fluid, such as air, may be hindered or substantially blocked from being conveyed through the platform 122 by the flap 128. In some embodiments, instead of a flap 128, the valve mechanism 124 may comprise a ball valve (not shown).

FIGS. 1A to 1D show the valve mechanism 124 of the body 106 in a substantially open state, in which air is free to flow through the platform 122 (as it is not blocked or largely inhibited by the open flap 128) and through the aperture 118. However, it will be appreciated that the valve mechanism 124 may also assume a closed state, in which air flow through the aperture 118 is hindered or inhibited by the closed flap 128). The flap 128 can readily deflect from a position in which it covers the aperture 118 over the platform 122 and blocks air flow there through, to a position in which it swings or pivots open while remaining attached to the cover portion 126 and thus allows air to pass through the aperture 118 and the platform 122. The flap 128 (and thus the valve mechanism 124) transitions between the open and closed states depending on whether the user 200 is inhaling (open) or exhaling (closed).

Figure 1B:
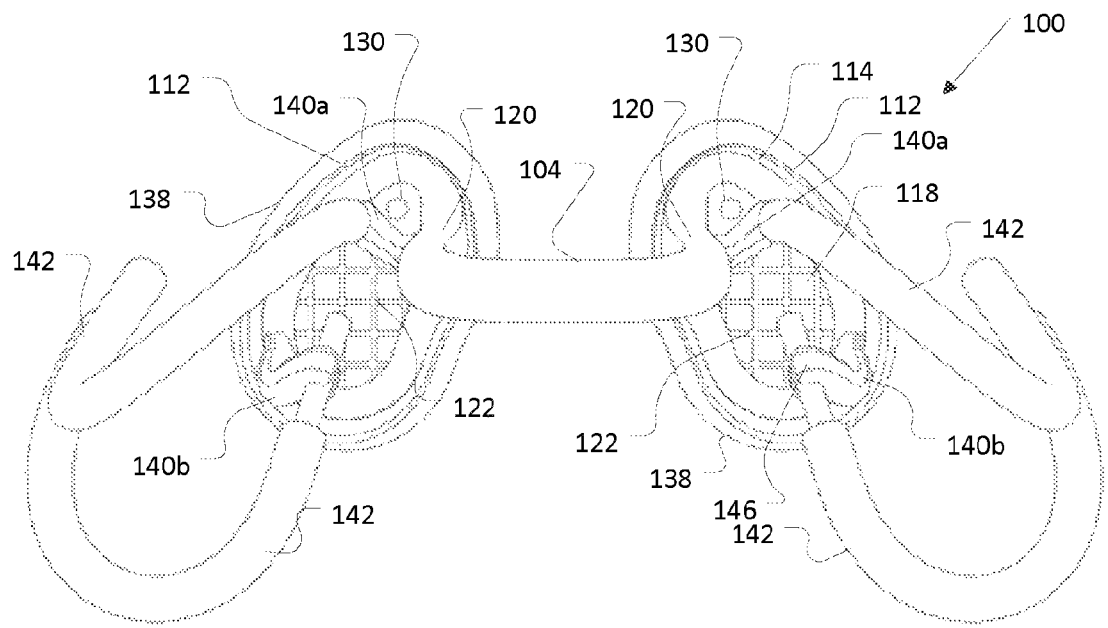
FIG. 1B is a front view of the nasal device of FIG. 1A.
Figure 1C:
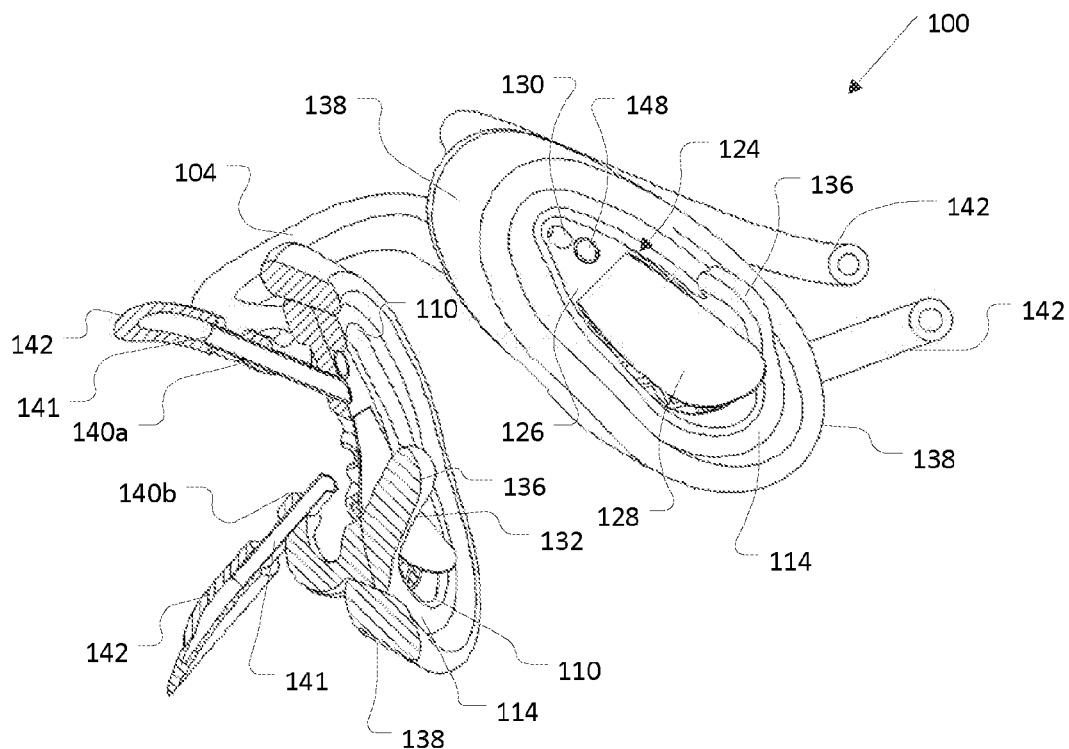
FIG. 1C is a back perspective view of the nasal device of FIG. 1A.
Figure 1D:
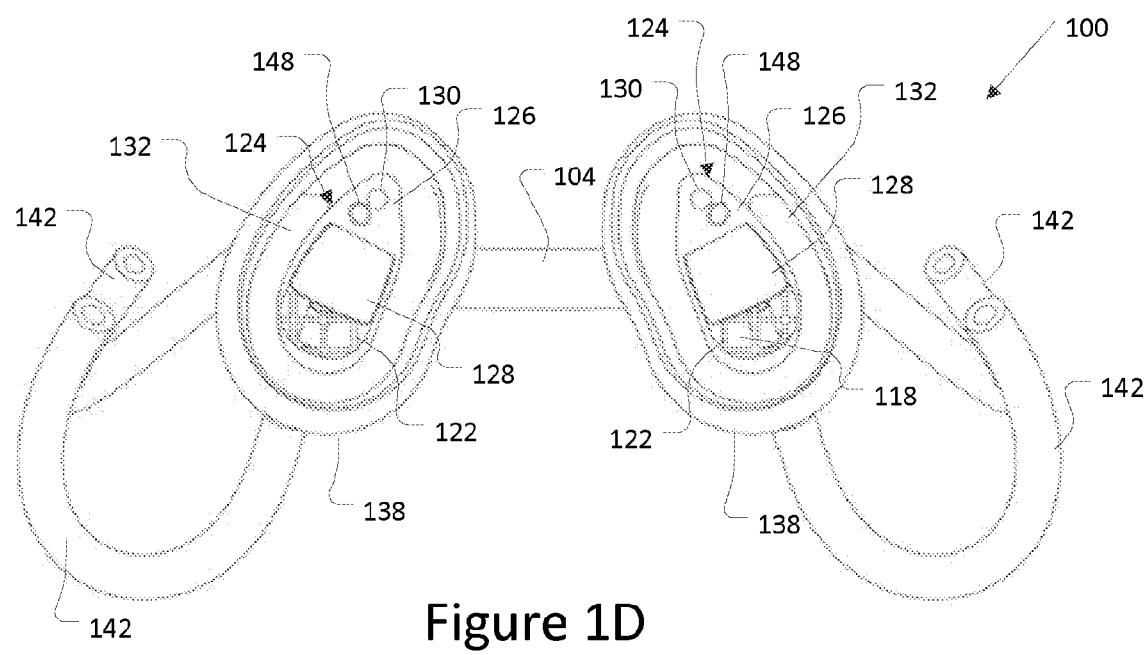
FIG. 1D is back view of the nasal device of FIG. 1A.

As shown in FIGS. 1B to 1D, an orifice 130 may be disposed in the cover portion 126 of the valve mechanism 124. The orifice 130 may allow passage of a small amount of air through the platform 122 and cover portion 126, for example, when the user is inhaling and exhaling. In some embodiments, the valve mechanism 124 may include an orifice adjustment mechanism (not shown) to allow for selective adjustment of a size or dimension of the orifice 130. For example, the orifice adjustment mechanism (not shown) may comprise a disc (not shown) configured to transition between an open state where the disc does not substantially occlude or close off the orifice 130 and fluid, such as air, may be conveyed through the orifice 130, a partially open state where the disc partially occludes or closes off the orifice 130 and a closed state, where the disc substantially occludes or closes off the orifice 130 to mitigate or hinder fluid, such as air, being conveyed through the orifice 130.

In some embodiments, the valve mechanism 124 may be configured to act as a one-way valve, for example, to allow fluid flow, for example, airflow, through the platform 122 substantially in a single direction only. In some embodiments, the valve mechanism 124 is configured to create a controllable and adjustable expiratory positive air pressure (EPAP) within the nasal cavity, or an intranasal positive expiratory airway pressure (INPEAP) and which may thereby assist in the treatment of sleep apnea, such as obstructive sleep apnea (OSA). The size of the orifice 130 may be selected to control or at least substantially influence EPAP within the nasal cavity 202 of the nose 204.

In some embodiments, one or both of the components 102 of the nasal device 100 may be dual dilation nasal dilator components 102. For example and as illustrated in FIGS. 1A to 1D, the body 106 may comprise an arm member 132 extending outwardly from the loop structure 108 and arranged to engage with a nostril 214 of the nose 204 of a user 200, as shown in FIGS. 2A and 2B. The outer surface 112 of the loop structure 108 may be configured for urging against a nasal passage wall 212 of the nasal cavity 202 to dilate nostrils 214 of the nose 204. In this way, the loop structure 108 and the arm member 132 of the nasal device 100 may cooperate as a dual dilation mechanism configured to perform dual or concurrent dilation of the nostril 214 of the user 200.

In some embodiments, the arm member 132 may extend from the first side 114 of the loop structure 108. The arm member 132 may be configured to extend along the nasal passage 208 of the nasal cavity 202 and engage with the internal surface of the nostril 214. The arm member 132 may have a first end 134 coupled to, for example, attached to or integrally formed with, the first side 114 of the loop structure 108 and a free end 136 opposite to the first end 134. In some embodiments, the arm member 132 may extend in a third plane P3 which may be substantially orthogonal to the first plane P1. In some embodiments, the first plane P1 may form a substantially acute angle, a substantially right angle or a substantially obtuse angle with the third plane P3.

In some embodiments, the arm member 132 may be configured to exert an outward force on the internal surface of the nostril 214 of the user 200 to thereby stent and/or dilate the nostril. For example, the arm member 132 may protrude outwardly beyond a perimeter of the loop structure 108 and/or may be resiliently biased to an outward deflecting configuration. In some embodiments, the arm member 132 may be flexible and resiliently biased away from the loop structure 108 to allow the arm member 132 to be compressed for insertion into the nose 204 of the user 200 and to reform once placed inside the nose 204 to thereby dilate the nostrils 214, as illustrated in FIGS. 2A and 2B. In use, the arm member 132 is configured to engage the internal surface of the nostril 214 at a junction of the greater alar cartilage and lateral nasal cartilage 216, when the nasal dilator 100 appropriately placed in the nostril 214, to thereby stent or dilate the nasal passage 208.

In some embodiments, the body 106 may comprise an outer layer 138 disposed along the outer surface 112 of the loop structure 108. For example, the outer layer 138 may extend along at least a section of a length of (and optionally all the way around) the outer surface 112 of the loop structure 108. The outer layer 138 may be arranged to follow a contour of the nasal cavity 202 of the user 200 and form a seal with the nasal passage wall 212 to substantially seal or block fluid flow, for example, airflow, between the outer surface 112 of the loop structure 108 of the body 106 and a nasal passage 208 of the nose 204 of the user 200. The outer layer 138 may comprise a deformable material, such as a memory foam or an over mould. The over mould may be infused with a medicament and/or a fragrance. The outer layer 138 may be formed of a soft elastomeric material, for example. A thickness of the outer layer 138 may be selected to accommodate a distance between the outer surface 112 of the loop structure 108 and the nasal passage 208 of a user 200. In some embodiments, the outer layer 138 may comprise a protruding double flange portion (not shown) extending along at least a section of a length of (and optionally all the way around) the outer surface 112 of the loop structure 108. In some embodiments, the outer layer 138 of the body 106 may comprise a deformable and optionally inflatable tube (not shown) extending along at least a section of a length of (and optionally all the way around) the outer surface 112 of the loop structure 108.

As illustrated in FIGS. 1A to 1D, one or both of the components 102 may comprise one or more mounts 140 extending from the body 106. The one or more mounts 140 may be configured to support and/or retain one or more conduits 142, such as tubes, to allow for the gathering of data and/or the delivery of fluids to or removal of fluids from the nasal cavity 202 of the user 200. Alternatively or in addition, the mounts 140 may be configured to support and/or retain one or more sensors (not shown) to allow for the gathering of data. In some embodiments, the one or more mounts 140 may be configured to receive a coupler 141 to allow the one or more mounts 140 to couple to one or more conduits 142 and/or sensors (not shown). For example, the coupler 141 may be substantially tubular to allow for fluid communication between the one or more conduits 142 and the coupler 141. In some embodiments, the one or more mounts 140 may comprise an elongate member 144 having a looped or bent end portion 146 which may be configured to grip or engage with the coupler 141 or directly with the conduit 142 or sensor (not shown) to hold it in a selected position.

In some embodiments, a first mount 140a may extend from the body 106. For example, the first mount 140a may extend from the leg member 120, from the second side 116 of the loop structure 108 and/or from the platform 122.

As shown in FIGS. 1A to 1D, a conduit aperture 148 may be disposed in the body 106. In some embodiments, the conduit aperture 148 may be disposed in the platform 122 and may extend therethrough. In some embodiments, the conduit aperture 148 may be disposed in the loop structure 108, and for example, may extend from the second side 116 of the loop structure 108 to the first side 114 of the loop structure 108. The conduit aperture 148 may be configured to cooperate with the first mount 140a to facilitate passage of fluid between the conduit aperture 148 and the coupler 141 and/or conduit 142 supported by the first mount 140a. In some embodiments, conduit aperture 148 may be configured to cooperate with the first mount 140a to accommodate passage of the conduit 142 or coupler 141 supported by the first mount 140a through the body 106.

In some embodiments, the body 106 may comprise a second mount 140b extending from the body 106. For example, the second mount 140b may extend from the leg member 120, from the second side 116 of the loop structure 108 and/or from the platform 122. In some embodiments, the second mount 140b may be configured to position an open end of the coupler 141 and/or conduit 142 in proximity to the nasal cavity 202.

Referring to FIGS. 2A and 2B, there is illustrated a user, generally indicated at 200, wearing the nasal device 100 of FIGS. 1A to 1D. As depicted, the nasal device 100 is configured to be orientated such that the body 106 of the first and second components 102 are received within a nasal cavity 202 of the nose 204 and the connector 104 spans a septum 206 of the nose 204 and the leg members 120 extend inward, along a nasal passage 208. In some embodiments, the nasal device 100 is configured to be orientated such that connector 104 spans the columella (the terminal section or fleshy external end of the septum) of the nose 204 and is positioned toward a tip 210 of the nose 204.

In some embodiments, the body 106 may be composed of a flexible material and may be generally squeezed or compressed by the user 200 into a compressed state to allow insertion of the body 106 into the nasal cavity 202 of the nose 204. The body 106 may be biased to reform or revert to a natural uncompressed state and once inserted into the nasal cavity 202 and the outer surface 112 of the loop structure 108 may urge against or exert an outward force on a nasal passage wall 212 of the nose 204 and may thereby dilate the nasal passage 208.

Referring now to FIGS. 3A to 3D, there is illustrated a nasal device, generally indicated at 300, including a first component 302 coupled to a second component 302, according to some embodiments. As shown in FIGS. 3A to 3D, the nasal device 300 may comprise similar features and elements to those of nasal device 100 as depicted in FIGS. 1A to 1D and accordingly those similar features and elements are denoted by like numerals.

As illustrated in FIGS. 3A to 3D, one or both of the components 302 may comprise one or more mounts 304 extending from the body 106. The one or more mounts 304 may be configured to support and/or retain one or more conduits 142 to allow for the gathering of data, diagnosis and/or the delivery of fluids to or removal of fluids from the nasal cavity 202 and/or delivery of drugs to the nasal cavity 202 of the user 200 and/or to support and/or retain one or more sensors to allow for the gathering of data and diagnosis purposes. In some embodiments, the one or more mounts 304 may be configured to receive a coupler 141 to allow the one or more mounts 304 to couple to one or more conduits 142 and/or sensors (not shown). For example, the coupler 141 may be substantially tubular to allow for fluid communication between the one or more conduits 142 and the coupler 141.

In some embodiments, the one or more mounts 304 may be provided on or supported by a mount assembly 306. For example, and as illustrated in FIGS. 3A to 3D, the mount assembly 306 may extend from the body 106. For example, the mount assembly 306 may extend from the second side 116 of the loop structure 108, the inner surface 110 of the loop structure 108 and/or from the platform 122. In some embodiments, the mount assembly 306 may be disposed on the platform 122 toward or in proximity to the orifice 130.

The mount assembly 306 may comprise an inner passage 308 which may define a cavity 309 and may be configured to convey fluid to and/or from the orifice 130. For example, the mount assembly 306 may be substantially tubular or sleeve-like in shape. The mount assembly 306 may be positioned such that the inner passage 308 aligns with, and/or is substantially coaxial with, the orifice 130 to allow for fluid communication between the inner passage 308 and the orifice 130.

In some embodiments, the one or more mounts 304 comprise a first mount 304a projecting or extending from the mount assembly 306. In some embodiments, the first mount 304a extends from the platform 122 and is supported by the mount assembly 306.

The first mount 304a may be configured to support at least one conduit 142, such as a tube, and/or a sensor (not shown). For example, the first mount 304a may comprise an inner passage 310 arranged to receive a conduit (not shown), a sensor (not shown) or a coupler 141 for coupling the first mount 304a to the conduit (not shown) and/or sensor (not shown). For example, the coupler 141 may be substantially tubular to allow for fluid communication between the one or more conduits 142 and the coupler 141. The first mount 304a may be substantially tubular or sleeve shaped. The conduit (not shown) or the coupler 141 may be configured to extend along at least a portion of the inner passage 310, and in some embodiments, along the entire length of the inner passage 310. The first mount 304a may be configured to cooperate with the conduit aperture 148 to accommodate passage of the conduit (not shown) or coupler 141 received by the first mount 304a to the conduit aperture 148 to facilitate the communication of fluid between the conduit (not shown) or coupler 141, the conduit aperture 148 and the nasal passage 208 of the user 200 in use. In some embodiments, the first mount 304a may be configured to cooperate with the conduit aperture 148 to accommodate passage of the conduit (not shown) or coupler 141 received by the first mount 304a through the body 106, for example, through the platform 122, or through the loop structure 108. For example, the inner passage 310 of the first mount 304a may be substantially aligned with or positioned coaxially with the conduit aperture 148.

In some embodiments, the one or more mounts 304 comprise a second mount 304b projecting or extending from the mount assembly 306. The second mount 304b may include an inner passage 312 arranged to receive a conduit (not shown), a sensor (not shown) or a coupler 141 for coupling to a conduit (not shown) and/or a sensor (not shown). The inner passage 312 of the second mount 304b may be in fluid communication with the inner passage 308 of the mount assembly 306. In some embodiments, the conduit (not shown) or coupler 141 received by the second mount 304b may extend along at least a portion of the inner passage 312 and in some embodiments, may extend into the inner passage 308 of the mount assembly 306.

By providing the nasal device 300 with the mount assembly 306, the nasal device 300 may accommodate the one or more mounts 304 more effectively than might be achieved by disposing the one or more mounts 302 directly on the body 106. For example, the mount assembly 306 may be configured to accommodate or support more mounts 304 than might be capable of being provided directly on the body 106 due to the limited space available.

Referring now to FIGS. 4A to 4D, there is illustrated a nasal device, generally indicated at 400, including a first component 402 coupled to a second component 402, according to some embodiments. The nasal device 400 may comprise similar features and elements to those of nasal device 100 as depicted in FIGS. 1A to 1D and accordingly those similar features and elements are denoted by like numerals.

As illustrated in FIGS. 4A to 4D, one or both of the components 402 of the nasal device 400 may comprise one or more mounts 404 extending from the body 106. The one or more mounts 404 may be configured to support and/or retain one or more conduits 142 to allow for the gathering of data and/or the delivery of fluids to or removal of fluids from the nasal cavity 202 of the user 200. Alternatively or in addition, the mounts 304 may be configured to support and/or retain one or more sensors (not shown) to allow for the gathering of data.

In some embodiments, the one or more mounts 404 may be provided on or supported by a mount assembly 406. The mount assembly 406 may comprise an inner passage 418 defining a cavity 420.

As illustrated in FIGS. 4A to 4D, the mount assembly 406 may comprise a collar or shroud 408 extending from the body 106. For example, a first end 408a of the collar 408 may be coupled to and may extend from the inner surface 110 or the second side 116 of the loop structure 108. In some embodiment, the first end 408a of the collar 408 may form a seal with the loop structure 108, for example, with the inner surface 110 or the second side 116 of the loop structure 108. In some embodiments, the collar 408 may be integrally formed with, or connected to, the valve mechanism 124 and the collar 408 may be removably coupled to the second side 116 or inner surface 110 of the loop structure 108.

In some embodiments, the collar 408 may comprise a narrowing or tapering section 410 to transition from the loop structure 108 to an end section 412 of the collar 408, which may define a smaller aperture than the aperture 118 defined by the loop structure 108.

In some embodiments, the one or more mounts 404 comprise a first mount 404a provided at or projecting from the mount assembly 406. For example, the first mount 404a may be disposed on the tapering section 410 and/or the end section 412.

The first mount 404a may be configured to support at least one conduit (not shown), such as a tube and/or a sensor (not shown). For example, the first mount 404a may comprise an inner passage 414 arranged to receive a conduit (not shown), a sensor (not shown) or a coupler 141 for coupling the first mount 404a to a conduit (not shown) and/or sensor (not shown). The coupler 141 may be substantially tubular to allow for fluid communication between the one or more conduits (not shown) and the coupler 141. The conduit (not shown) or the coupler 141 may be configured to extend along at least a portion of the inner passage 414, and in some embodiments, along the entire length of the inner passage 414 and into the cavity 420 of the mount assembly 406.

Figure 4A:
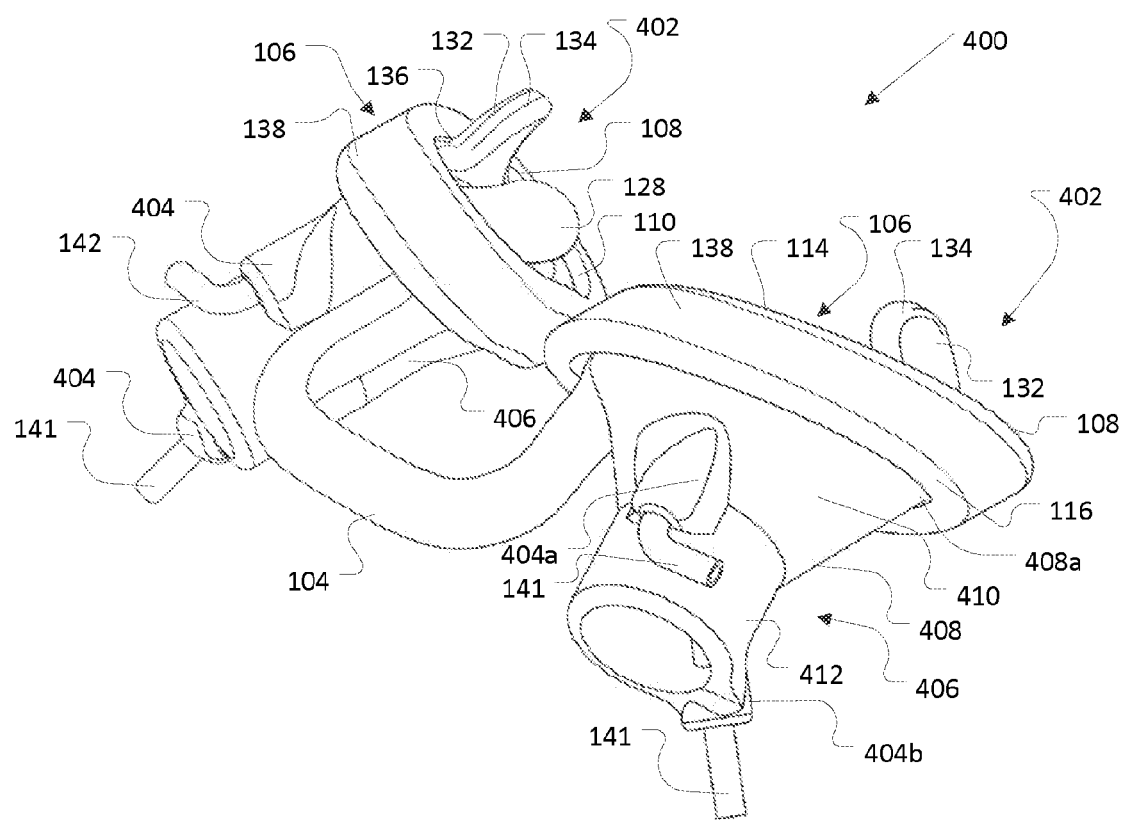
FIG. 4A is a front perspective view of a nasal device according to some embodiments.
Figure 4B:
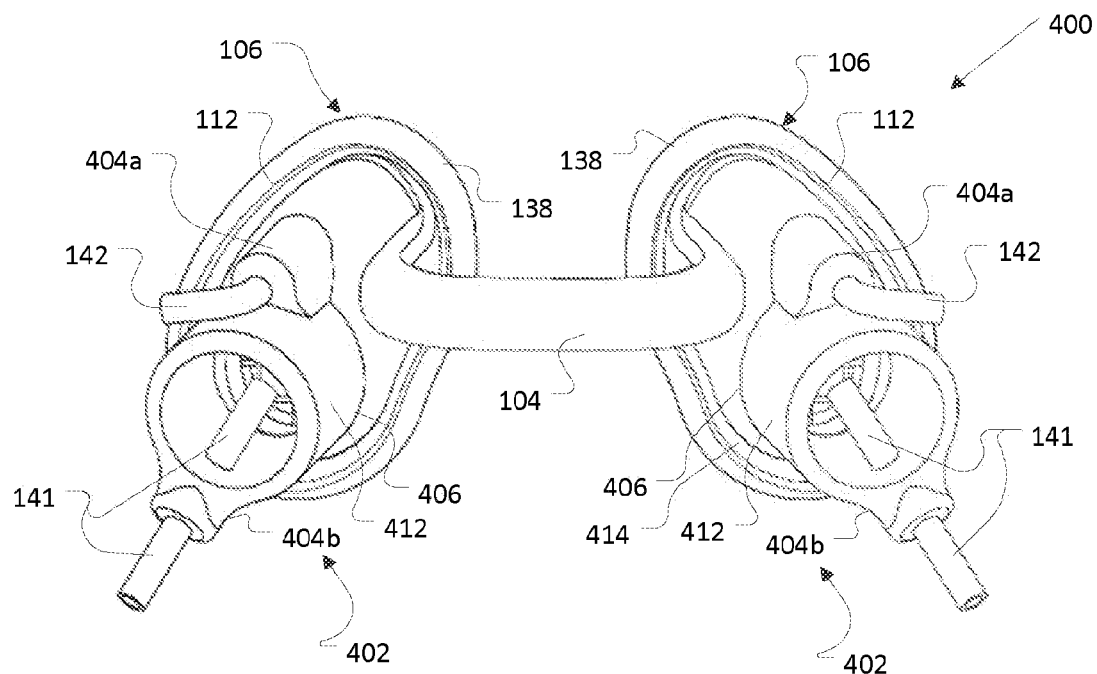
FIG. 4B is a front view of the nasal device of FIG. 4A.
Figure 4C:
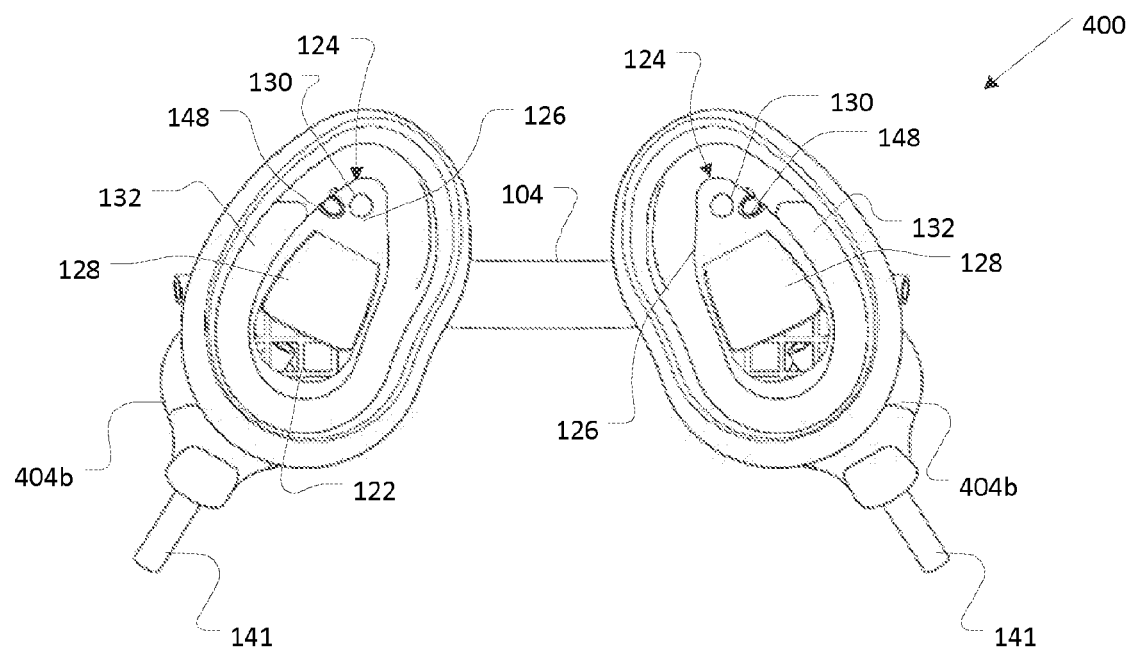
FIG. 4C is back view of the nasal device of FIG. 4A.
Figure 4D:
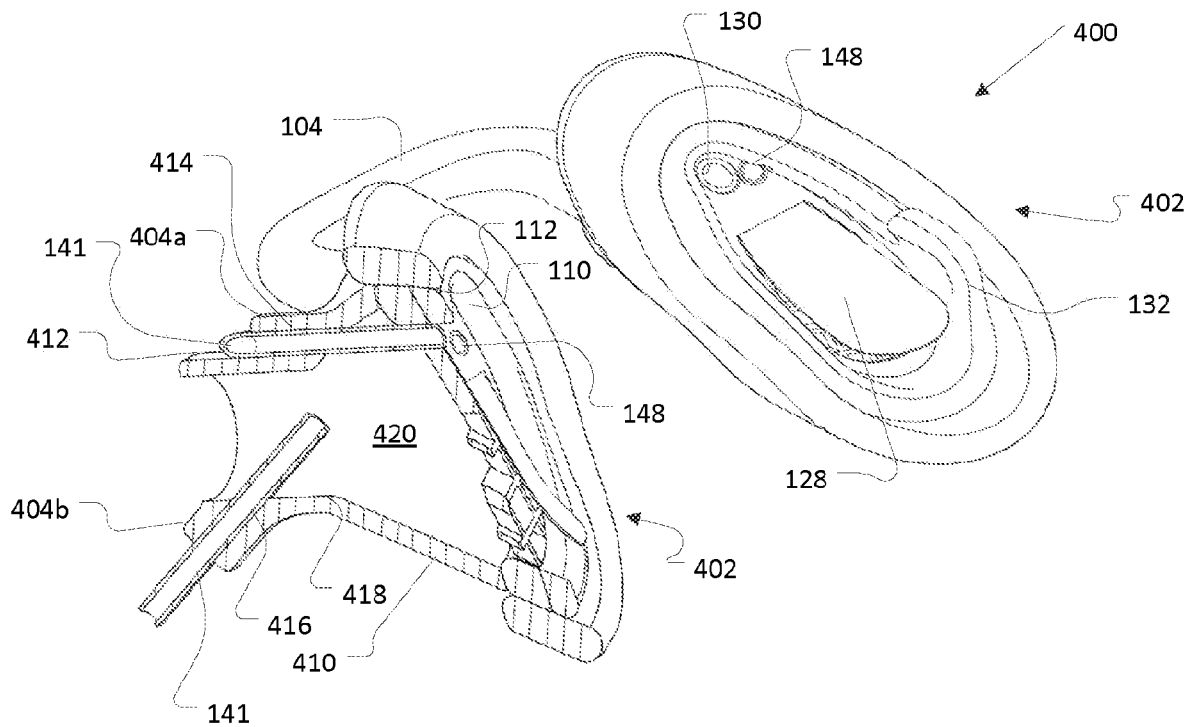
FIG. 4D is a back perspective view of the nasal device of FIG. 4A showing a cut away view of a component of the nasal device.

The first mount 404a may be configured to cooperate with the conduit aperture 148 to accommodate passage of the conduit (not shown) or coupler 141 received by the first mount 404a to the conduit aperture 148, for example, to facilitate communication of fluid between the conduit (not shown) or coupler 141, the conduit aperture 148 and the nasal passage 208 of the user 200 in use. In some embodiments, the first mount 404a may be configured to cooperate with the conduit aperture 148 to accommodate passage of the conduit (not shown) or coupler 141 received by the first mount 404a through the body 106, for example, through the platform 122, or through the loop structure 108. For example, the inner passage 414 of the first mount 404a may be substantially aligned with or positioned coaxially with the conduit aperture 148, as best shown in FIG. 4D.

In some embodiments, the one or more mounts 404 may comprise a second mount 404b provided at or projecting from the mount assembly 406. The second mount 404b may be configured to support at least one conduit (not shown), such as a tube and/or a sensor (not shown). For example, the second mount 404b may include an inner passage 416 arranged to receive a conduit (not shown), a sensor (not shown) or a coupler 141 for coupling the second mount 404b to a conduit (not shown) or a sensor (not shown). The inner passage 416 of the second mount 404b may be in fluid communication with the inner passage 418 of the mount assembly 406. In some embodiments, the conduit 142 or the coupler 141 supported by the second mount 404b may extend along at least a portion of the inner passage 416 and in some embodiments, may extend into the inner passage 418 and cavity 420 of the mount assembly 406.

By providing the nasal device 400 with the mount assembly 406, the nasal device 400 may accommodate the one or more mounts 404 more effectively than might be achieved by disposing the one or more mounts 404 directly on the body 106. For example, the mount assembly 406 may be configured to accommodate or support more mounts 404 than might be capable of being provided directly on the body 106 due to the limited space available.

Figure 5:
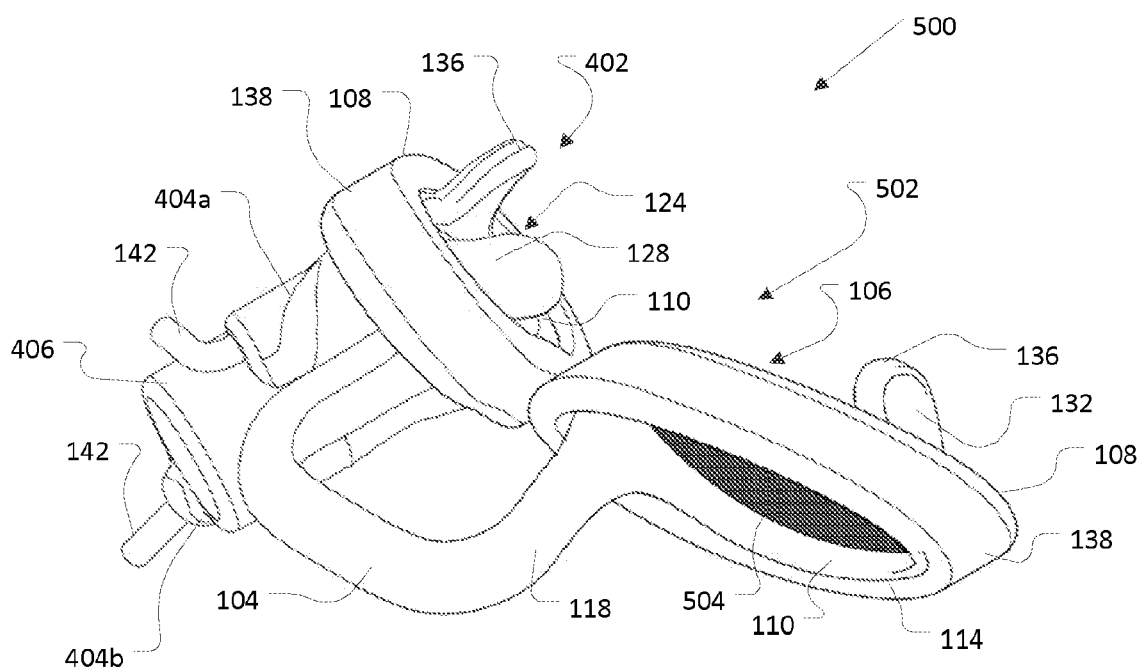
FIG. 5 is a perspective view of a hybrid nasal device, according to some embodiments.

Referring to FIG. 5, there is illustrated a hybrid nasal device 500 comprising a body 106 of the nasal device 400 and a component 502. As illustrated, the component 502 may comprise similar features and elements to those of nasal device 100 as depicted in FIGS. 1A to 1D and accordingly those similar features and elements are denoted by like numerals. However, instead of the platform 122 and the valve mechanism 124 of nasal device 100, the component 502 comprises a body 106 having a barrier 504 which spans the aperture 118 of the loop structure 108 to substantially block or mitigate the flow of fluid through the aperture 118. In other embodiments, the component 402 of nasal device 500 may be replaced with the component 102 of nasal device 100 or the component 302 of nasal device 300.

In some embodiments, the conduit 142 may comprise a cannula and may be configured for delivering and/or removing fluid from the nasal cavity 202 of a user 200 and/or gathering data using the device 100, 300, 400, 500. In some embodiments, the conduit 142 may comprise a pitot tube (not shown) or other suitable pressure measurement instrument for measuring fluid flow velocity of the breath of a user wearing the device 100, 300, 400, 500.

In some embodiments, as discussed above, the one or more mounts 140, 304, 404 of the devices 100, 300, 400 may be configured to support one or more sensors (not shown), such as pressure sensors or solid probe sensors. For example, the one or more sensors may comprise an array of force sensitive cells or silicon-based piezoresistive pressure sensors, which when supplied with an electrical potential, a sensor output signal is generated that is proportional to a pressure applied to the array. In some embodiments, the one or more sensors may be configured to transmit the output signal to a receiver (not shown) wirelessly or via an electrical connector, such as a wire, coupled to both the at least one sensor (not shown) and the receiver (not shown). For example, the electrical connector may be disposed within and carried by a conduit 142.

When a user 200 donning the device 100, 300, 400, 500 inhales atmospheric gases through the nose 204, the flap 128 of the cover portion or seal 126 is forced to an open state and gases flow through the seal 126 and aperture 118 of the components 102, 302, 402, 502 of the device 100, 300, 400, 500 and may also flow through the orifice 130. When the user 200 exhales, atmospheric gases exert a force on the seal 126 causing the flap 128 to assume a substantially closed state and obstructing gases from exiting the nasal passage 208 through the flap 128. Consequently, the gases are forced or directed to exit the nasal passage 208 through the orifice 130. In some embodiments, the degree or extent of EPAP and speed of orifice exhalation will depend on the size of the orifice 130.

Figure 6:
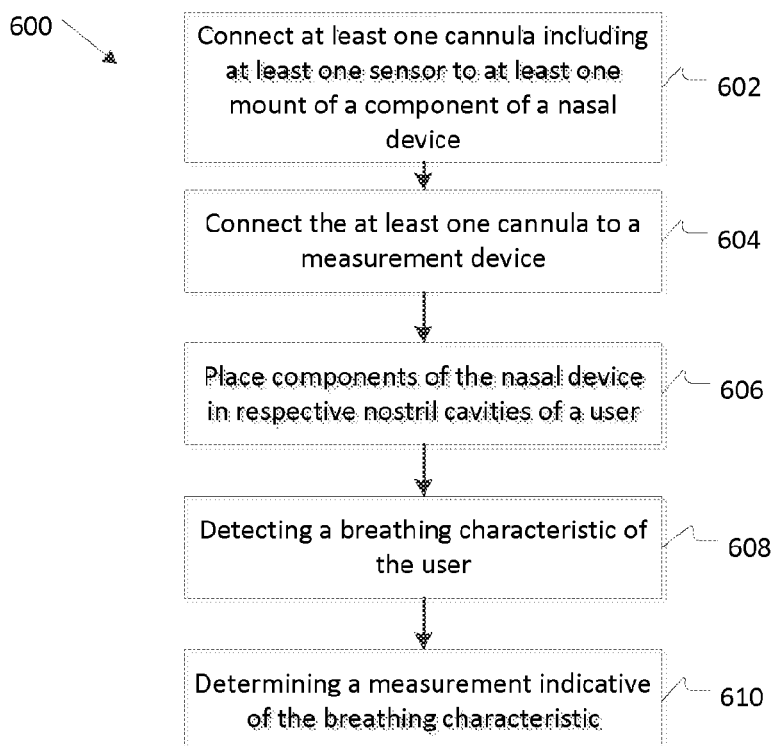
FIG. 6 is a process flow diagram showing a method of gathering of data from a user wearing the device of any one of FIG. 1A, 3A, 4A or 5.

Some embodiments relate to a method 600 of gathering of data from a user wearing the device 100, 300, 400, 500, as depicted in the process flow diagram of FIG. 6. The method 600 comprises coupling at least one sensor to at least one mount of the device 100, 300, 400, 500, at 602. For example, the at least one sensor may be coupled to or disposed within a first conduit or cannula 142 and a first end of the first cannula 142 may be directly connected, or connected via a coupler 141 to a first mount 140a, 304a, 404a. In some embodiments, a second sensor may be coupled to or disposed within a second conduit or cannula 142 and a first end of the second cannula 142 may be directly connected, or connected via a coupler 141 to a second mount 140b, 304b, 404b.

The method 600 comprises connecting a second end of the at least one cannula 142 to a measurement device (not shown), at 604. For example, the measurement device (not shown) may comprise a manometer or other instrument capable of measuring air pressure, air velocity, temperature or air volume. The first and second components 102, 302, 402, 502 are inserted into respective nasal cavities 202 of a user's nose 204, at 606.

The method 600 further comprises detecting at the one or more sensors a breathing characteristic of the user, at 608 and determining at the measurement device (not shown) a measurement indicative of the breathing characteristic of the user, at 610. For example, the breathing characteristic may comprise at least one of air flow, air pressure and air volume. In some embodiments, the first cannulas 142 is employed to detect air pressure within the nasal cavity 202 of the user 200 and the second cannula 142 is employed to detect a rate of air flow external of the nasal cavity 202 of the user 200. For example, a sensor (not shown), such as an EPAP sensor, may be connected to the first cannula 142 coupled to the first mount 140a, 304a, 404a to detect an amount of pressure exerted at an open end of the coupler 141 in close proximity to the conduit aperture 148 and a pitot tube (not shown) may be disposed within the second cannula 142 coupled to coupler 141 of the second mount 140b, 304b, 404b of the nasal dilator 100, 300, 400 and may be configured to measure a rate of air flow travelling close to or in a vicinity of an open end of the coupler 141, substantially external to the nasal cavity 202.

In some embodiments, only one of the first or second cannulas 142 is employed to gather or measure data associated with the user 200 wearing the device 100, 300, 400, 500 and the other of the first or second cannulas 142 is employed to deliver fluids to the nasal cavities 202 or remove fluids from the nasal cavities 202.

Figure 7:
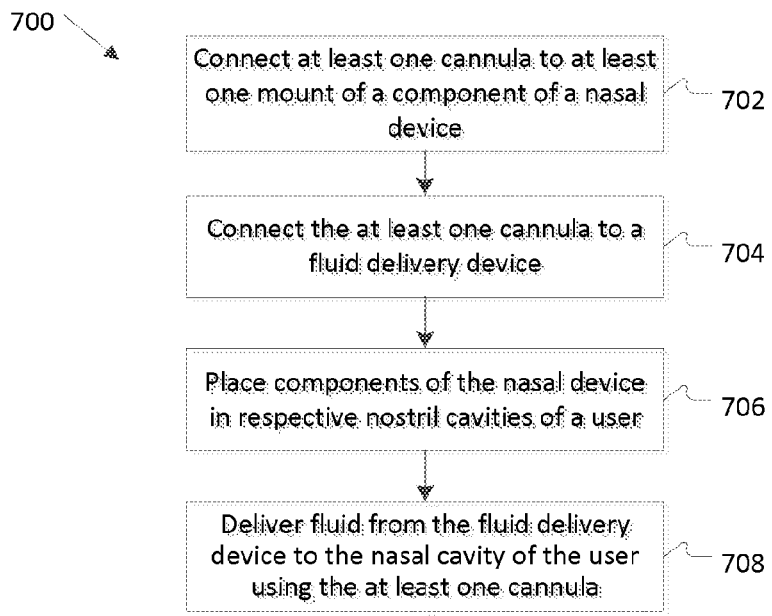
FIG. 7 is a process flow diagram showing a method of delivering fluids to a nasal cavity of a user wearing the device of any one of FIG. 1A, 3A, 4A or 5.

Some embodiments relate to a method 700 of delivering fluids to a nasal cavity 202 of a user 200 wearing the device 100, 300, 400, 500, as depicted in the process flow diagram of FIG. 7. The method 700 comprises connecting at least one cannula 142 to at least one mount of the device 100, 300, 400, 500, at 702. For example, a first end of a first cannula 142 may be directly connected, or connected via a coupler 141 to a first mount 140a, 304a, 404a. In some embodiments, a first end of a second cannula 142 may be directly connected, or connected via a coupler 141 to a second mount 140b, 304b, 404b. The method 700 comprises connecting a second end of the at least one cannula 142 to a fluid delivery device (not shown), at 704. For example, the fluid delivery device (not shown) may comprise a pump. The first and second components 102, 302, 402, 502 are inserted into respective nasal cavities 202 of a user's nose 204, at 706. The method 700 further comprises delivering fluids from the fluid deliver device (not shown) to the nasal cavity of the user 200 using the one or more cannulas 142, at 708. In some embodiments, only one of the first or second cannulas 142 is employed to deliver fluids to the nasal cavity 202 and the other of the first or second cannulas 142 is employed to remove fluids from the nasal cavity 202 and/or to gather or measure data associated with the user 200 wearing the device 100, 300, 400, 500, such as fluid flow velocity of the breath of the user 200.

Figure 8:
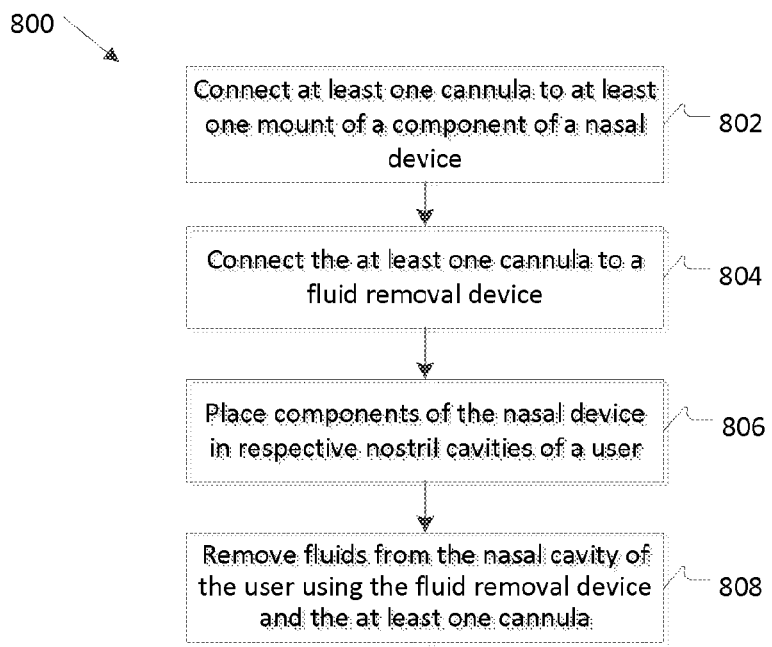
FIG. 8 is a process flow diagram showing a method of removing fluids from a nasal cavity of a user wearing the nasal device of any one of FIG. 1A, 3A, 4A or 5.

Some embodiments relate to a method 800 of removing fluids from a nasal cavity 202 of a user 200 wearing the device 100, 300, 400, 500, as depicted in the process flow diagram of FIG. 8. The method 800 comprises connecting at least one cannula 142 to at least one mount of the device 100, 300, 400, 500, at 802. For example, a first end of a first cannula 142 may be directly connected, or connected via a coupler 141 to a first mount 140a, 304a, 404a. In some embodiments, a first end of a second cannula 142 may be directly connected, or connected via a coupler 141 to a second mount 140b, 304b, 404b. The method 800 comprises connecting a second end of the at least one cannula 142 to a fluid removal device (not shown), at 804. For example, the fluid removal device (not shown) may comprise a suction pump, either manually or electronically controlled. The first and second components 102, 302, 402, 502 are inserted into respective nasal cavities 202 of a user's nose 204, at 806. The method 800 further comprises removing fluids from at least one of the nasal cavities of the user 200 using the fluid removal device (not shown) and the one or more cannulas 142, at 808. In some embodiments, only one of the first or second cannulas 142 is employed to remove fluids from the nasal cavity 202 and the other of the first or second cannulas 142 is employed to deliver fluids to the nasal cavity 202 and/or to gather or measure data associated with the user 200 wearing the device 100, 300, 400, 500, such as fluid flow velocity of the breath of the user 200.

Figure 9:
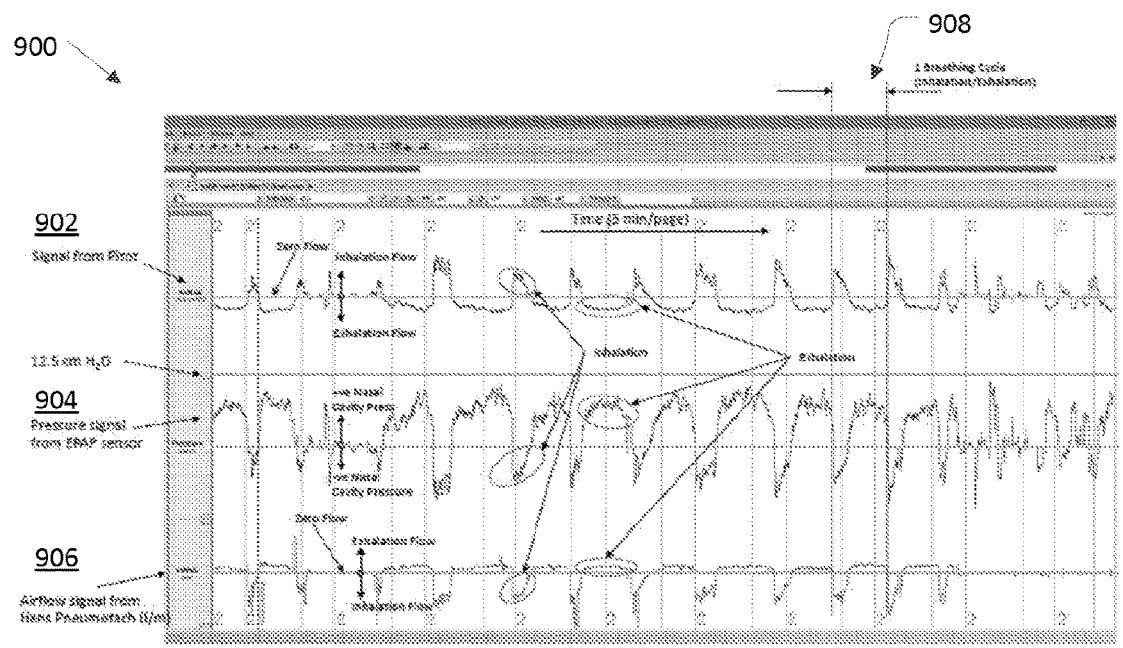
FIG. 9 is a graphical representation of measurements from a user wearing the nasal device of FIG. 4A.

Referring now to FIG. 9, there is shown a graphical representation 900 over a period of time of 5 mins of measurements from a user 200 wearing the nasal device 400 of FIGS. 4A to 4D and a pneumotach face mask (not shown). The graphical representation 900 shows air flow rate, at 902, measured using a pitot tube disposed in a first cannula 142 supported by the first mount 404a, air pressure, at 904, measured using a EPAP sensor disposed in a second cannula 142 supported by the second mount 404b and air inhaled and exhaled through both nose and mouth, at 906, measured by the pneumotach face mask (not shown) connected to the user 200.

The pitot tube is configured to measure a rate of air flow travelling past the end of the cannula 142 substantially external to the nasal cavity 202 of the user 200. The EPAP sensor is configured to measure air pressure within the nasal cavity 202. Both the pitot tube and the EPAP sensor are connect via the cannulas 142 to an air pressure transducer and an air diaphragm, for receiving, recording and outputting signals of flow rate and pressure respectively. The pneumotach mask is configured to measure an amount of air flow inhaled and exhaled by the user through their nose and mouth during normal breathing. This measured airflow may then be compared to the airflow measured by the pitot tube 902.

As depicted within a window 908 of FIG. 9, upon inhalation by the user 200, air pressure measured by the EPAP sensor rapidly decreases as inhaled gas travels into the nasal cavity 202 and a negative pressure is recorded. Upon inhalation by the user 200, the rate of air flow measured by the pitot tube rapidly increases to a peak. Upon exhalation by the user 200, air pressure measured by the EPAP sensor rapidly increases to reach a maximum positive pressure reading and substantially levels out for a period of time until internal gases escape through the orifice 130, causing the pressure to decrease to a negative pressure value before a next inhalation. On exhalation, airflow rate measured by the pitot tube substantially steadily decreases to a substantially zero value. The airflow rate substantially steadily decreases due to a majority of the exhaled gases being obstructed by the closed flap 128 of the device 400 and some slow and steady airflow escaping via the orifice 130.

Figure 10:
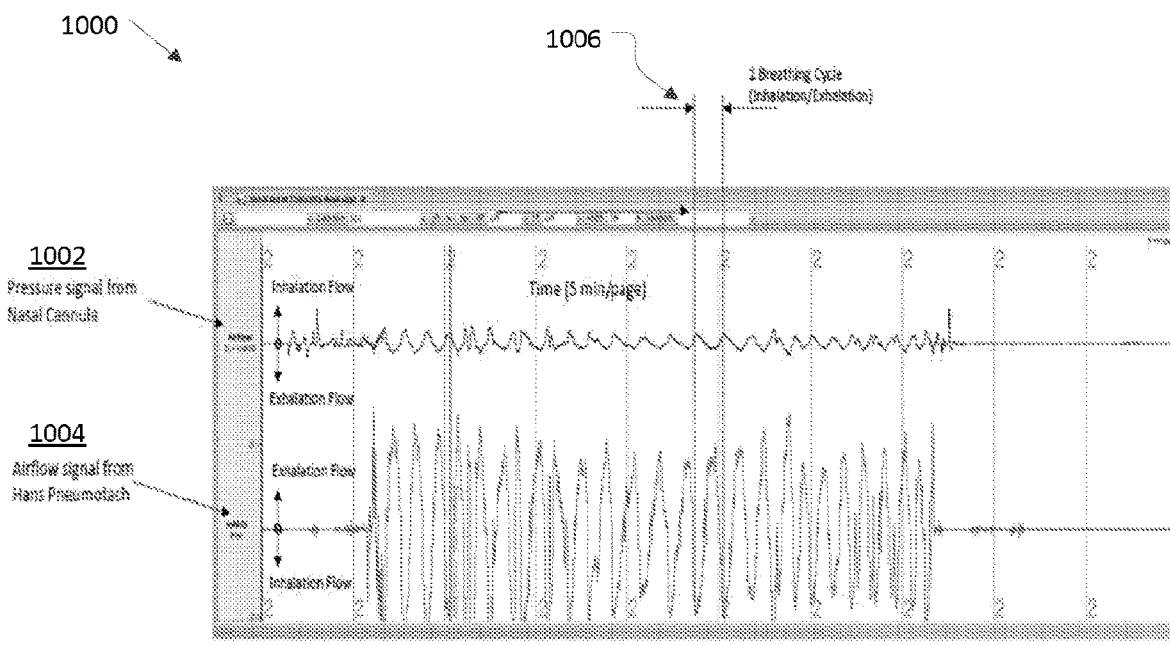
FIG. 10 is a graphical representation of measurements from a user wearing a known nasal cannula assembly and a pneumotach face mask.

FIG. 10 shows a graphical representation 1000 over a period of time of 5 minutes of measurements from the same user 200 who is wearing a known nasal cannula assembly (not shown) configured to measure air flow rate and monitor for stable, normal breathing patterns. The user 200 is also wearing a pneumotach face mask (not shown) configured to measure air being inhaled and exhaled through both the nose 204 and mouth. The graphical representation 1000 shows air flow rate at 1002 measured using a cannula tube of the nasal cannula assembly disposed in the nose 204 of the user 200 and also shows the inhalation and exhalation flow rate of the user at 1004 as measured by the pneumotach face mask.

From a comparison of the two graphical representations 900 and 1000, and in particular windows 908 and 1006, it is clear that the device 400 substantially and significantly alters breathing parameters of the user 200. For example, the device causes a significant increase in EPAP upon nasal exhalation due to the closure of the flap 128 on the platform 122 of the device 400 and the cause of nasally exhaled air to be emitted from only the orifice 130. The graphical representation 900 confirms the ability of the device 400 to record its respective measurements while being worn by a user 200.

A clinical study has been performed in order to evaluate the intranasal positive expiratory airway pressure device 100 of FIG. 1A to 1D for efficacy and tolerability in participants with moderate OSA and snoring. This study was approved by the Monash Health Human Research Ethics Committee (Melbourne Australia)

Intranasal positioning of the device 100 is designed to both stent the anterior nasal airway and deliver positive expiratory airway pressure, pneumatically splinting the upper airway during expiration while allowing near normal inspiratory flow. It is hypothesised that the intranasal positioning of the device 100 is secure, comfortable and facilitates anterior nasal dilatation.

Method: The device 100 of FIG. 1A to 1D is configured for insertion into the anterior nares and allows near normal inspiratory resistance and near normal inspiratory resistance and increased expiratory resistance while also pneumatically splinting the oropharynx.

Participants for the study were recruited from sleep disordered breathing clinics according to the following criteria:
 a. Inclusion criteria: Aged 18-75 years, moderate severity OSA (apnea hypopnea index, AHI, 15-29) established via polysomnography (PSG) within the previous 2 months, bed partner able to provide a subjective assessment of snoring severity.
 b. Exclusion criteria: Pregnancy, excessive sleepiness requiring urgent treatment, non-obstructive sleep disordered breathing, significant comorbidities, inability to provide consent, any anatomical reasons that precluded the wearing of the device.

Participants with moderate OSA were enrolled prospectively. A period of observation for one week was performed with a diary documenting sleep habits and partner supplied snoring severity on an visual analogue scale (1-10). A therapeutic PSG with participants using a prototype device was performed. For the study, the device 100 was customised to include extra cannula that measure intranasal pressure and flow without modifying the valve characteristics. In particular, a first cannula associated with a pressure sensor was connected to the first mount of the device 100 and a second sensor associated with a flow sensor was connected to the second mount of the device 100. Studies were scored using AASM 2012 rules.

Following the diagnostic study, participants were discharged with fourteen days of prototype single use devices with graded resistance; 3 days of low resistance, 3 days of medium resistance and 8 days of treatment resistance to acclimatise participants. Subjective sleep information was recorded as well as comfort and snoring.

The efficacy of the device 100 was analysed using a paired t-test for statistical significance. Responders were defined as having an apnea hypopnea index (AHI) reduction of >50% and/or AHI <5 events per hour. Partial responders were defined as having reduction in AHI between 30-50%.

Results: Twenty seven participants were recruited from Monash Health. Eight participants withdrew from the study prior to their implementation. Nineteen participants completed the diagnostic PSG and went on to trial the devices at home. Table 1 below shows the demographic characteristics of these participants.

TABLE 1

Demographics (Brackets refer to standard deviation)

| | |
|---|---|
| Participants | 19 |
| Age | 50.6 (+/−14) |
| Male | 14 [74%] |
| BMI | 27.7 (+/−8) |
| Neck Circumference | 39.3 (+/−4) |
| ESS | 8.5 (+/−4) |
| AHI | 19.2 (+/−3) |

Response to the treatment was variable with some significant responders and some in which OSA appeared to deteriorate. The mean AHI reduced non significantly from 19.2/hr to 16.5/hr. Similar non-significant reductions were demonstrated in supine NREM sleep (AHI 35.2/hr to 30.9/hr) and REM sleep (AHI 22.0 to 17.5/hr). Lateral NREM AHI increased from 7.7/hr to 11.2/hr. These results are summarised in Table 2 below.

TABLE 2

AHI results

| | Baseline | Treatment |
|---|---|---|
| AHI | 19.2 | 16.5 |
| Supine NREM | 35.2 | 30.9 |
| Lateral REM | 7.7 | 11.2 |
| REM | 22.0 | 17.5 |

Figure 11:
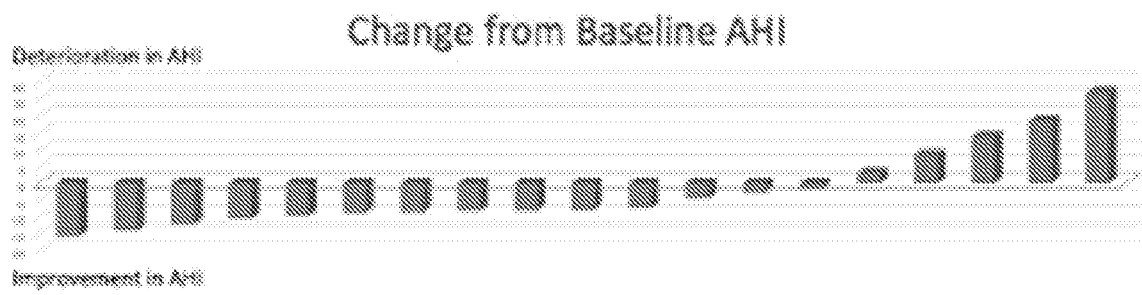
FIG. 11 is a graphical representation of a change in apnea hypopnea index (AHI) from a baseline per patient participating in a clinical study.
Figure 12:
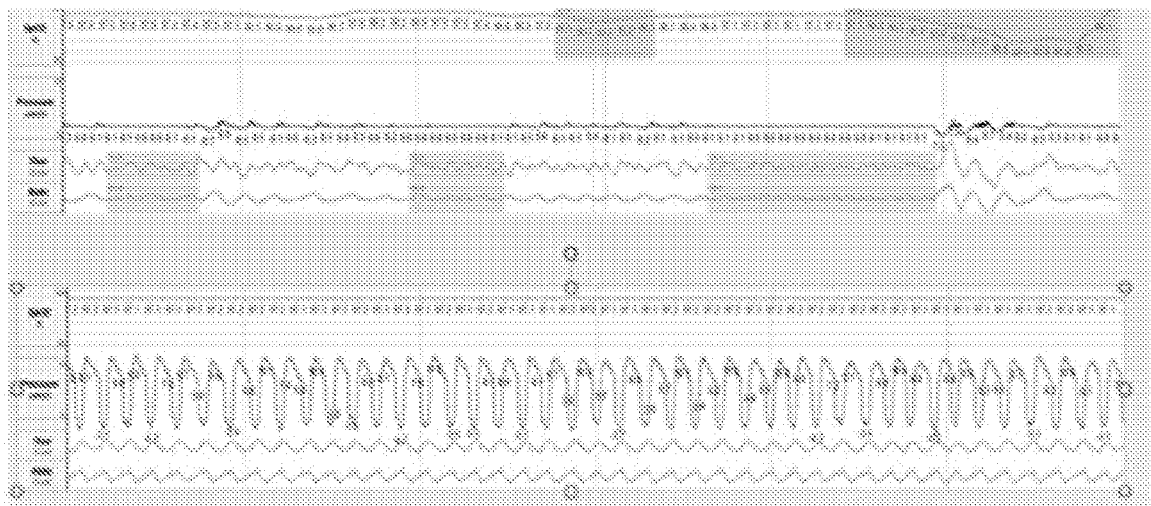
FIG. 12 displays two graphical representations of measurements of intranasal pressure from a user wearing the device of FIGS. 1A to 1D.

Seven out of 19 participants were responders. As shown in FIG. 11, five participants were partial responders and a further 7 participants showed no response or a deterioration. Four of the 7 participants that showed no improvement or deterioration were shown to mouth breathe significantly across the night. Mouth breathing was not identified in any of the responders, as shown in FIG. 12. In particular, FIG. 12 displays two stacked graphical representations of measurements from a user wearing the device 100. In the upper representation, the results reflect a situation where the user was asked to breathe only through the mouth and not through the nose. In the lower representation, the results reflect a situation where the user was asked to breathe only through the nose and not through the mouth. The graphical representation shows a change in intranasal pressure, measured in cmH20. Of key relevance is that users which are habitual mouth breathers did not activate a change in their intranasal pressures. The lower graph demonstrates that correct nasal breathing results in an increase in intranasal pressures of up to 11 cmH20, whereas mouth breathers show ineffective pressures of <1 cmH20.

Device usage across all participants was 75% with four participants unable to tolerate using the device for the fourteen days available for usage. Comfort was cited as the most common reason for poor tolerance of this device.

Subjective assessments of snoring and sleep revealed a modest reduction in snoring severity as assessed by the bed partner with an increase in self assessed sleep time, as shown in Table 3 below

TABLE 3

Usage & Tolerability

| | Pre | Post |
|---|---|---|
| Sleep (Hours) | 6.14 | 6.38 |
| Bed (Hours) | 7.32 | 7.15 |
| Snore (Partner Reported 1-10) | 4.81 | 4.09 (ns) |
| Snore (responders) | 4.50 | 3.10 (ns) |
| Overal Usage (hrs/night) | | 4.79 |
| Tolerated until 14 days | | 14 (78%) |

Discussion: This study suggests that the InPEAP device 100 may effectively treat some patients with moderate severity obstructive sleep apnoea but not all. The study suggests that the device was well tolerated in most of the participants but that an alteration or variation of materials will likely improve patient comfort for even greater tolerability for periods of use over 10 days. The study suggests that target patients are those that are habitually breath through their nose. Inclusion of such patients only in further trials are expected to more significantly support the positive results of this trial.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. A nasal device comprising:
a first component and a second component; and
a connector for coupling the first component to the second component and configured to span a nasal septum of the user;
wherein the first component comprises:
a body configured for insertion into a nasal cavity of a nose of a user, the body comprising:
a loop structure having an inner surface defining an aperture and a reverse outer surface, the loop structure being configured for alignment with an interior contour of a nasal passage of the nose;
a platform spanning the aperture defined by the inner surface of the loop structure; and
a valve mechanism disposed on the platform for controlling fluid flow through the aperture;
wherein a conduit aperture is disposed in the body;
a first mount extending from the body and (i) a first conduit or (ii) a first coupler for coupling a first conduit to the first mount, the first conduit or first coupler being supported by the first mount and the conduit aperture being configured to cooperate with the first mount to accommodate passage of the first conduit or first coupler through the body and into the nasal cavity to facilitate passage of fluid through the first conduit;
a second mount extending from the body and (i) a second conduit or (ii) a second coupler for coupling a second conduit to the second mount, the second conduit or second coupler being supported by the second mount such that an open end of the second conduit or second coupler is positioned in proximity to the nasal cavity.

2. The nasal device of claim 1, wherein the second component comprises a body configured for insertion into a nasal cavity of a nose of a user, the body comprising a loop structure having an inner surface defining an aperture and a reverse outer surface, the loop structure being configured for alignment with an interior contour of a nasal passage wall of the nose and a barrier which spans the aperture of the loop structure to mitigate the flow of fluid through the aperture.

3. The nasal device of claim 1, wherein the valve mechanism comprises a seal spanning the aperture defined by the inner surface of the loop structure, wherein the seal includes a valve configured to transition between an open state, whereby fluid may be conveyed through the platform, and a closed state, whereby fluid may be hindered from being conveyed through the platform by the valve.

4. The nasal device of claim 1, wherein the conduit aperture is disposed in the platform and extends therethrough.

5. The nasal device of claim 1, wherein the conduit aperture is disposed in the loop structure and extends from a first side of the loop structure to a reverse second side of the loop structure.

6. The nasal device of claim 1, wherein the first component further comprises a mount assembly extending from the body and wherein at least one of the first and second mounts is supported by the mount assembly.

7. The nasal device of claim 6, wherein the second mount projects from the mount assembly, the second mount having an inner passage extending through the second mount and the inner passage of the second mount being in fluid communication with the inner passage of the mount assembly.

8. The nasal device of claim 6, wherein the mount assembly comprises a collar having a first end coupled to the body, the collar spanning the aperture defined by the inner surface of the loop structure and providing fluid communication between the aperture and the inner passage of the mount assembly.

9. The nasal device of claim 8, wherein the collar comprises a tapering section coupled to the body and an end section extending from the tapering section away from the body, wherein the tapering section forms a seal with at least one of the loop structure, the valve mechanism and the platform.

10. The nasal device of claim 1, wherein the first component further comprises a mount assembly for supporting at least one of the first and second mounts, the mount assembly having an inner passage extending through the mount assembly and the mount assembly being disposed on the body to allow for fluid communication between an orifice disposed in the platform and the inner passage.

11. The nasal device of claim 10, wherein the first mount projects from the mount assembly, the first mount having an inner passage extending through the first mount and configured to cooperate with the conduit aperture disposed in the body to facilitate passage of fluid between the conduit aperture and the first conduit.

12. The nasal device of claim 11, wherein the inner passage of the first mount is configured to cooperate with the conduit aperture to accommodate passage of the first conduit; or the first coupler through the body and into the nasal cavity.

13. The nasal device of claim 1, wherein the body further comprises
an arm member having a first end coupled to the loop structure and a free end, the arm member extending outwardly from the loop structure and configured to extend along a nasal passage of the nasal cavity and engage with an internal surface of a nostril of the nose.

14. The nasal device of claim 13, wherein the connector comprises a leg member extending outwardly from the loop structure and configured to protrude from the nasal cavity of the user, and wherein the arm member extends from a first side of the loop structure and the leg member extends from the reverse second side of the loop structure.

15. The nasal device of claim 1, wherein the loop structure comprises an outer layer disposed along at least a portion of the outer surface of the loop structure.

16. The nasal device of claim 15, wherein the outer layer is a deformable material comprising at least one of memory foam, an overmould, and an inflatable tube.

17. The nasal device of claim 15, wherein the outer layer comprises at least one protruding flange portion extending along at least a section of the outer surface of the loop structure.

18. The nasal device of claim 15, wherein the outer layer is infused with at least one of a compound, a medicament, a fragrance, and an aromatic agent.

19. A method of creating an intranasal positive expiratory airway pressure in a nasal cavity of a subject, the method comprising:
inserting the bodies of respective first and second components of the nasal device of claim 3 into respective nasal cavities of the subject such that the loop structure is aligned with an interior contour of a nasal passage of the nose and the valve mechanism is orientated to allow fluid flow through the valve in response to the subject inhaling and to substantially block fluid flow through the valve in response to the subject exhaling.

20. A method of gathering data from a user wearing the nasal device of claim 1, the method comprising:
coupling at least one cannula including at least one sensor to the at least one mount of a component of a nasal device;
coupling the at least one cannula to a measurement device;
inserting the components of the nasal device in respective nostril cavities of a user;
detecting by the at least one sensor a breathing characteristic of the user; and
determining by the measurement device a measurement indicative of the breathing characteristic.

* * * * *